(12) United States Patent
Shepherd et al.

(10) Patent No.: US 12,109,272 B2
(45) Date of Patent: Oct. 8, 2024

(54) INTERMITTENT DOSING OF GLUCOCORTICOID RECEPTOR MODULATORS FOR THE TREATMENT OF OVARIAN AND OTHER CANCERS

(71) Applicant: Corcept Therapeutics Incorporated, Menlo Park, CA (US)

(72) Inventors: Stacie Shepherd, Menlo Park, CA (US); Joseph K. Belanoff, Menlo Park, CA (US)

(73) Assignee: Corcept Therapeutics Incorporated, Redwood City, CA (US)

( * ) Notice: Subject to any disclaimer, the term of this patent is extended or adjusted under 35 U.S.C. 154(b) by 0 days.

(21) Appl. No.: 17/902,701

(22) Filed: Sep. 2, 2022

(65) Prior Publication Data
US 2023/0091637 A1     Mar. 23, 2023

Related U.S. Application Data

(60) Provisional application No. 63/345,682, filed on May 25, 2022, provisional application No. 63/324,873, (Continued)

(51) Int. Cl.
*A61K 47/64* (2017.01)
*A61K 31/337* (2006.01)
(Continued)

(52) U.S. Cl.
CPC .......... *A61K 47/643* (2017.08); *A61K 31/337* (2013.01); *A61K 31/4745* (2013.01); *A61P 15/00* (2018.01); *A61P 35/00* (2018.01)

(58) Field of Classification Search
CPC .............. A61K 31/4745; A61K 31/445; A61K 31/451; A61K 47/643; A61K 31/337; A61P 35/00; A61P 15/00
See application file for complete search history.

(56) References Cited

U.S. PATENT DOCUMENTS

2020/0197381 A1* 6/2020 Greenstein ........... C12Q 1/6886
2021/0147472 A1   5/2021 Fantin et al.

FOREIGN PATENT DOCUMENTS

WO   2017216772 A2   12/2017
WO   2021163273 A1   8/2021

OTHER PUBLICATIONS

Dhillon, S. Bevacizumab Combination Therapy: A Review of its Use in Patients with Epithelial Ovarian, Fallopian Tube, or Primary Peritoneal Cancer. BioDrugs 27, 375-392 (2013). https://doi.org/10.1007/s40259-013-0043-4 (Year: 2013).*
Golub et al. Molecular classification of cancer: class discovery and class prediction by gene expression monitoring. Science. Oct. 15, 1999;286(5439):531-7. doi: 10.1126/science.286.5439.531. PMID: 10521349. (Year: 1999).*
(Continued)

*Primary Examiner* — Kortney L. Klinkel
*Assistant Examiner* — Padmaja S Rao
(74) *Attorney, Agent, or Firm* — Kilpatrick Townsed & Stockton LLP

(57) ABSTRACT

Methods and compositions for treating cancer (e.g., ovarian, fallopian tube, uterine, cervical, vaginal, vulvar, or peritoneal cancer) are disclosed. The methods include intermittent administration of a glucocorticoid receptor modulator (GRM), such as a non-steroidal GRM (e.g., relacorilant), which may be orally administered, along with a cancer chemotherapy agent (such as, e.g., bevacizumab) to the patient. The GRM may be administered: at intervals separated by at least one day without GRM administration; by a schedule linked to the cancer chemotherapy schedule (e.g., a weekly chemotherapy regimen); on the day of, or the day before, or the day after, chemotherapy administration; by combinations thereof; and/or on other days. Ovarian cancer patients receiving intermittent relacorilant administration along with nab-paclitaxel administration had improved overall survival, improved progression free survival, improved duration of response, and other benefits as compared to
(Continued)

patients not receiving relacorilant while receiving nab-paclitaxel.

14 Claims, 17 Drawing Sheets

Related U.S. Application Data filed on Mar. 29, 2022, provisional application No. 63/244,825, filed on Sep. 16, 2021.

(51) Int. Cl.
*A61K 31/4745* (2006.01)
*A61P 15/00* (2006.01)
*A61P 35/00* (2006.01)

(56) References Cited

OTHER PUBLICATIONS

McClung et al. Int J Womens Health. 2016 8 59-75 (Year: 2016).*
Veneris et al., High glucocorticoid receptor expression predicts short progression-free survival in ovarian cancer, Gynecologic Oncology, vol. 146, 153-160, Apr. 26, 2017 (Year: 2017).*
International Patent Application No. PCT/US2022/042475 , "International Search Report and the Written Opinion", Dec. 21, 2022, 13 pages.
Stringer-Reasor et al., "Glucocorticoid Receptor Activation Inhibits Chemotherapy-Induced Cell Death in High-Grade Serous Ovarian Carcinoma", Gynecologic Oncology, vol. 138, No. 3, Sep. 2015, pp. 656-662.
International Patent Application No. PCT/US2022/042475 , "International Preliminary Report on Patentability", Mar. 28, 2024, 8 pages.

* cited by examiner

Efficacy Analysis – data cut-off 22 March 2021

Efficacy Analysis

| | INTERMITTENT | | CONTINUOUS | | COMPARATOR | |
|---|---|---|---|---|---|---|
| | Overall (N=60) | Primary Platinum Refractory Removed (N=53) | Overall (N=58) | Primary Platinum Refractory Removed (N=55) | Overall (N=60) | Primary Platinum Refractory Removed (N=53) |
| Progression-free survival*, median (95% CI), months | 5.55 (3.68, 7.20) | 5.55 (3.68, 7.29) | 5.29 (3.84, 5.55) | 5.29 (3.84, 5.55) | 3.75 (3.52, 5.36) | 3.75 (3.52, 5.36) |
| HR vs Comparator, (95% CI) | 0.66 (0.44, 0.98) | 0.64 (0.42, 0.98) | 0.83 (0.56, 1.22) | 0.83 (0.56, 1.23) | N/A | N/A |
| P-value | 0.04 | 0.03 | 0.33 | 0.34 | N/A | N/A |
| Objective response rate, n (%) | 20 (33.7%) | 19 (35.8%) | 19 (35.2%) | 19 (34.5%) | 19 (35.8%) | 9 (32.2%) |
| P-value | 0.99 | 0.69 | 0.97 | 0.79 | N/A | N/A |
| Duration of response*, median (95% CI), months | 5.55 (3.75, 5.88) | 5.55 (3.75, 5.88) | 3.79 (2.33, 5.59) | 3.79 (2.33, 5.55) | 3.65 (2.88, 5.09) | 3.65 (2.88, 5.09) |
| HR vs Comparator, (95% CI) | 0.36 (0.16, 0.77) | 0.36 (0.16, 0.77) | 0.72 (0.33, 1.58) | 0.72 (0.33, 1.58) | N/A | N/A |
| P-value | 0.006 | 0.006 | 0.42 | 0.42 | N/A | N/A |
| Overall survival*, median (95% CI), months | 12.94 (9.13, –) | 12.94 (11.89, –) | 11.30 (7.59, –) | 11.30 (7.59, –) | 10.41 (6.41, 16.76) | 10.41 (7.72, 16.76) |
| HR vs Comparator, (95% CI) | 0.60 (0.35, 1.14) | 0.55 (0.29, 1.03) | 1.07 (0.62, 1.85) | 1.00 (0.57, 1.76) | N/A | N/A |
| P-value | 0.124 | 0.059 | 0.813 | 0.99 | N/A | N/A |

* Kaplan-Meier estimate
CONTINUOUS, once-daily relacorilant + nab-paclitaxel; INTERMITTENT, intermittent relacorilant + nab-paclitaxel; COMPARATOR, nab-paclitaxel monotherapy

FIG. 7A

Subgroup: Results from Patients without Primary Platinum-Refractory Disease, who had from 1 to 3 Prior Lines of Therapy

|  | Intermittent Relacorilant + Nab-paclitaxel (N=46) | Nab-paclitaxel Monotherapy (N=50) |
|---|---|---|
| PFS[1] |  |  |
| Number of events, (%) | 36 (78.3%) | 48 (96.0%) |
| Median PFS (95% CI), months | 5.6 (3.7, 7.3) | 3.8 (3.5, 5.4) |
| HR (95% CI) | 0.58 (0.37, 0.91) | — |
| Log-rank test, P-value[2] | 0.016 | — |
| DoR[1] in patients with objective response |  |  |
| Number of patients with objective response | 18 | 17 |
| Number of events (%) | 13 (72.2%) | 16 (94.1%) |
| Median DoR (95% CI), months | 5.6 (3.8, 5.9) | 3.6 (1.9, 3.8) |
| HR (95% CI) | 0.26 (0.11, 0.62) | — |
| Log-rank test, P-value[2] | 0.001 | — |
| OS[3] |  |  |
| Number of events, (%) | 29 (63.0%) | 43 (86.0%) |
| Median OS (95% CI), months | 13.9 (11.1, 18.4) | 12.2 (7.7, 15.3) |
| HR (95% CI) | 0.52 (0.31, 0.86) | — |
| Log-rank test, P-value[2] | 0.01 | — |

[1]Data cutoff date for the primary analysis: March 22, 2021; applies to PFS and DoR.
[2]P-values are nominal, no multiplicity adjustment applied.
[3]Data cutoff date for the final (OS) analysis: March 7, 2022.

FIG. 7B

Intermittent Relacorilant Administration vs. Comparator

Subgroup: Excludes Primary Platinum-Refractory Patients and Patients with Four or More Prior Lines of Therapy Overall Survival – data cut-off 7 March 2022

Subgroup: Results from Patients without Primary Platinum-Refractory Disease, who had from 1 to 3 Prior Lines of Therapy Which Prior Therapy Included BEVACIZUMAB Therapy

|  | Intermittent Relacorilant + Nab-paclitaxel (N=25) | Nab-paclitaxel Monotherapy (N=31) |
|---|---|---|
| PFS[1] | | |
| Number of events, (%) | 20 (80.0%) | 30 (96.8%) |
| Median PFS (95% CI), months | 7.3 (3.7, 7.7) | 3.7 (2.2, 5.3) |
| HR (95% CI) | 0.40 (0.21, 0.77) | — |
| Log-rank test, *P*-value[2] | 0.005 | — |
| | | |
| DoR[1] in patients with objective response | | |
| Number of patients with objective response | 10 | 9 |
| Number of events (%) | 7 (70.0%) | 9 (100.0%) |
| Median DoR (95% CI), months | 5.6 (3.7, NR) | 3.1 (1.3, NR) |
| HR (95% CI) | 0.29 (0.09, 0.99) | — |
| Log-rank test, *P*-value[2] | 0.016 | — |
| | | |
| OS[3] | | |
| Number of events, (%) | 15 (60.0%) | 25 (80.6%) |
| Median OS (95% CI), months | 17.9 (12.8, NR) | 12.6 (6.4, 15.3) |
| HR (95% CI) | 0.38 (0.17, 0.82) | — |
| Log-rank test, *P*-value[2] | 0.011 | — |

[1]Data cutoff date for the primary analysis: March 22, 2021; applies to PFS and DoR.
[2]*P*-values are nominal, no multiplicity adjustment applied.
[3]Data cutoff date for the final (OS) analysis: March 7, 2022.
NR, not reached.

FIG. 7D

Initial Analysis - data cut-off 22 March 2021

The Safety and Tolerability of Intermittent Relacorilant + Nab-Paclitaxel is Comparable to Nab-Paclitaxel Monotherapy

| n, (%) | INTERMITTENT N=60 | CONTINUOUS N=57 | COMPARATOR N=60 | OVERALL N=177 |
|---|---|---|---|---|
| Neutropenia[a] | 12 (20.0%) | 22 (38.6%) | 22 (36.7%) | 56 (31.6%) |
| Grade ≥3 | 4 (6.7%) | 15 (26.3%) | 9 (15.0%) | 28 (15.8%) |
| Febrile neutropenia (Grade 3)[b] | 0 (0.0%) | 0 (0.0%) | 1 (1.7%) | 1 (0.01%) |
| Anemia[c] | 29 (48.3%) | 37 (64.9%) | 34 (56.7%) | 100 (56.5%) |
| Grade ≥3 | 8 (13.3%) | 11 (19.3%) | 7 (11.7%) | 26 (14.7%) |
| Peripheral neuropathy[d] | 21 (35.0%) | 27 (47.4%) | 18 (30.0%) | 66 (37.3%) |
| Grade ≥3 | 0 (0.0%) | 9 (15.8%) | 3 (5.0%) | 12 (0.07%) |
| Fatigue or asthenia | 33 (55.0%) | 41 (71.9%) | 39 (65.0%) | 113 (96.6%) |
| Grade ≥3 | 6 (10.0%) | 5 (8.8%) | 1 (1.7%) | 12 (0.07%) |

[a] Neutropenia, neutrophil count decreased; [b] Secondary to E.coli urinary sepsis in this patient; [c] Anemia, hemoglobin decreased; [d] Neuropathy peripheral, neurotoxicity, peripheral motor neuropathy, peripheral sensorimotor neuropathy, peripheral sensory neuropathy
CONTINUOUS, once-daily relacorilant + nab-paclitaxel; INTERMITTENT, intermittent relacorilant + nab-paclitaxel; COMPARATOR, nab-paclitaxel monotherapy; G-CSF, granulocyte-colony stimulating factor

- All relacorilant-treated patients received prophylactic G-CSF per protocol to reduce the risk of neutropenia
- 46.7% of patients in the comparator arm received G-CSF per the investigator's standard practice

FIG. 8

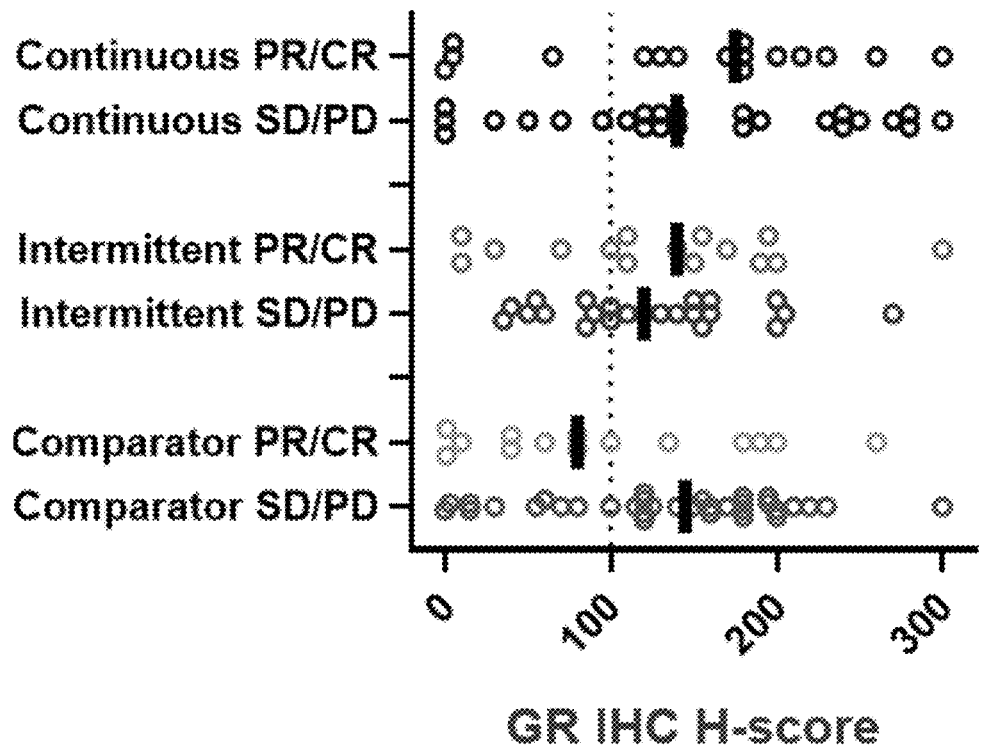
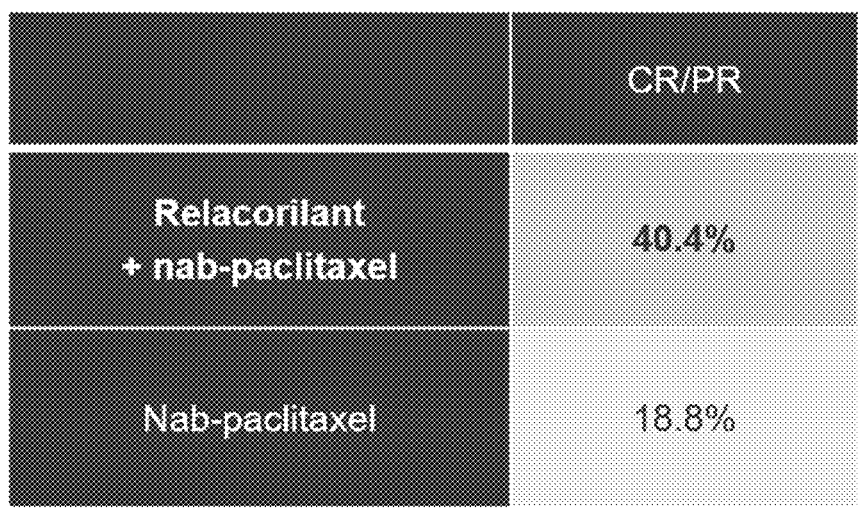
FIG. 9A

Arm A: continuous relacorilant+NP

Arm B: intermittent relacorilant+NP

Arm C: NP alone

SGK1: serum and glucocorticoid regulated kinase 1

GSK3B: Glycogen synthase kinase 3 beta

PIK3CG: Phosphatidylinositol-4,5-Bisphosphate 3-Kinase Catalytic Subunit Gamma

INTERMITTENT DOSING OF GLUCOCORTICOID RECEPTOR MODULATORS FOR THE TREATMENT OF OVARIAN AND OTHER CANCERS

CROSS-REFERENCE TO RELATED APPLICATIONS

This application claims priority to, and the benefit of, U.S. Provisional Patent Application No. 63/244,825, filed Sep. 16, 2021; U.S. Provisional Patent Application No. 63/324,873, filed Mar. 29, 2022; U.S. Provisional Patent Application No. 63/345,682, filed May 25, 2022; and international application PCT/US2021/050617, filed Sep. 16, 2021, all of which applications are each hereby incorporated by reference herein in their entireties.

BACKGROUND

Glucocorticoid receptors ("GR") are present in almost all bodily tissues. Cortisol, an endogenous hormone which acts via GR, affects many biological systems, and may play a role in the progression of cancer. For example, cortisol and GR-mediated signaling can affect inflammation, and can affect the immune system. However, it is not clear whether such effects promote or inhibit cancer growth. Although many tumor types express GR, and GR expression is high in some tumors (e.g., ovarian cancer tumors), the effects of modulating GR-mediated signaling pathways on cancer progression and cancer treatment are unclear, and the importance of GR-mediated signaling pathways in cancer progression and cancer treatment is unresolved.

Cancers such as ovarian, fallopian tube, uterine, cervical, vaginal, and vulvar cancer, and other cancers of female reproductive organs and tissues, as well as peritoneal cancer, are a significant fraction of cancers afflicting women (peritoneal cancer rarely afflicts men). These and other cancers may be hormone-sensitive.

Such cancers are often diagnosed only at an advanced stage. Therapeutic options are limited and the outlook for these cancer patients is poor. Conventional treatment options for such cancers include surgery and chemotherapy (radiation therapy (also termed "radiotherapy") is rarely used for such patients). Although in some cases such cancers may be resectable at the time of diagnosis, most patients with these cancers are treated with chemotherapy, such as platinum-based chemotherapy. Chemotherapeutic agents typically rely upon causing generalized damage to DNA and destabilization of chromosomal structure which may reduce cancer cell proliferation, promote or induce tumor-cell apoptosis, and may eventually lead to destruction of cancer cells.

Ovarian cancer, for example, can be a devastating disease. Although the majority of ovarian cancer patients initially respond to chemotherapy (which is often platinum-based chemotherapy), recurrence of the cancer is high, with the vast majority of ovarian cancer patients relapsing (Kemp et al., Int J Women's Health 5:45-51 (2013): around 80% relapse within 18 months; Luvero et al., Crit Rev Oncol/Hematol 140:28-38 (2019)). Unfortunately, the chemotherapy response rate in these relapsed patients may be low, and may provide only a short period of progression-free survival period (Luvero et al., Therap Adv Med Oncol 6(5):229-239 (2014)). Less than a year of overall survival after relapse is the norm for recurrent ovarian cancer.

Further therapies are limited for platinum-resistant ovarian cancer patients; only a small fraction of such patients respond to standard chemotherapy treatments (Luvero et al. 2014). Further treatment options include surgery, chemotherapy, molecularly targeted agents (antiangiogenic agents and PARP inhibitors, and radiation. (alone or in combination). For relapsed patients receiving initial therapy for recurrent platinum-resistant ovarian cancer, paclitaxel, liposomal doxorubicin, topotecan, given as single agents or combined with bevacizumab, or, the combination of gemcitabine plus carboplatin are approved and the most commonly used therapies in this setting (Luvero, 2014; Pujade-Lauraine, et al. J Clin Oncol 37:2437-2448 (2019)). Chemotherapy plus bevacizumab has shown the best results in patients who received less than two prior regimens, did not have refractory disease, and had no history of a bowel obstruction within six months of treatment (Pujade-Lauraine et al., J Clin Oncol 32:1302-1308 (2014)). For platinum-resistant ovarian cancer patients or those with refractory disease, the standard of care is limited to sequential use of chemotherapy not previously administered. However, outcomes for these further chemotherapeutic options are generally poor.

There is a large unmet need for effective, well-tolerated treatments for ovarian cancer, cervical cancer, vaginal cancer, vulvar cancer, fallopian tube cancer, uterine cancer, and other tumors of the female reproductive organs and tissues, as well as for peritoneal cancer. There is a large unmet need for effective, well-tolerated treatments for women with platinum-resistant ovarian cancer.

SUMMARY

Disclosed herein are novel methods for treating cancers, and novel uses of glucocorticoid receptor modulator (GRM) compounds, such as nonsteroidal GRMs, including heteroaryl-ketone fused azadecalin compounds, for treating cancers.

Applicant discloses methods of treating cancer which comprise intermittently administering a GRM to a cancer patient who is receiving cancer chemotherapy. The GRM may be administered orally. The methods include intermittently administering an effective amount of a GRM to a patient hosting a cancer, that patient being in need of, and receiving, cancer chemotherapy treatment for the cancer; the cancer chemotherapy treatment comprises administration of a cancer chemotherapy agent according to a cancer chemotherapy dosing schedule that includes at least one day without administration of the cancer chemotherapy agent between days of cancer chemotherapy agent administration. As disclosed herein, intermittent GRM administration comprises at least a first round of GRM administration and a second round of GRM administration, with at least one day without GRM administration separating the first round and the second round. The first round of GRM administration may be administration of a GRM on one day; or on two consecutive days; or on three consecutive days; or on more consecutive days. The second round of GRM administration may be administration of a GRM on one day; or on two consecutive days; or on three consecutive days; or on more consecutive days. The first round and the second round need not have the same number of days.

Intermittent GRM administration to a patient also receiving cancer chemotherapy may comprise administration of the GRM on days coordinated with the schedule of administration of the cancer chemotherapy. A round of GRM administration may be administered on a day related to, or may be administered on a day determined by, the cancer chemotherapy dosing schedule for the patient. For example, a round of GRM administration may be administered to the patient before, at the time of (e.g., on the same day as), or after the patient receives a dose of chemotherapy agent.

In embodiments, a round of GRM administration may be begun, or completed, one or more days before a day on which the patient is administered chemotherapy agent. In embodiments, a round of GRM administration may be begun, or completed, on a day on which the patient is administered chemotherapy agent. In embodiments, a round of GRM administration may be begun, or completed, one or more days after the patient is administered chemotherapy agent.

Applicant further discloses uses of a GRM for use in treating cancer according to the methods disclosed herein. For example, such uses comprise intermittently administering the GRM to a cancer patient who is being administered a cancer chemotherapy agent on multiple days, according to a dosing schedule that requires at least one day with no administration of the cancer chemotherapy agent to the patient, between days on which the cancer chemotherapy agent is administered to the patient. Intermittent GRM administration to a patient also receiving cancer chemotherapy may comprise administration of the GRM on days coordinated with the schedule of administration of the cancer chemotherapy. In embodiments, intermittent GRM administration includes administration of the GRM on the same day that the cancer chemotherapy agent is administered to the patient. Intermittent GRM administration may include administration of the GRM on one or more days when the cancer chemotherapy agent is not administered to the patient. Intermittent GRM administration may include administration of the GRM on the same day that the cancer chemotherapy agent is administered to the patient, and on one or more days when the cancer chemotherapy agent is not administered to the patient.

In embodiments, the GRM is a nonsteroidal GRM. In aspects of the methods and uses disclosed herein, the nonsteroidal GRM is a compound comprising a heteroaryl ketone fused azadecalin structure; in embodiments, the GRM is a heteroaryl ketone fused azadecalin structure disclosed in U.S. Pat. No. 8,859,774 (the contents of which is are hereby incorporated by reference in its entirety). The heteroaryl-ketone fused azadecalin GRM may be relacorilant, which is (R)-(1-(4-fluorophenyl)-6-(1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone ("relacorilant", having the following structure:

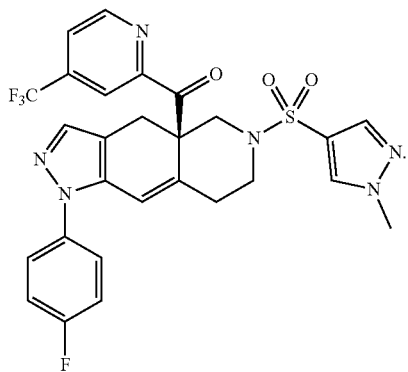

Relacorilant is also known as CORT125134; it is disclosed as Example 18 of U.S. Pat. No. 8,859,774.

Cancer chemotherapy agents, as used herein, include all anti-neoplastic agents, such as chemotoxic compounds and formulations that are typically toxic to cancer cells (and often non-cancerous cells as well), antiproliferative agents, anti-metastatic agents, and, include antibodies, checkpoint inhibitors, and other agents and treatments that inhibit, stop, or reverse the growth or spread of cancer in a cancer patient, alone or in conjunction with other agents. The cancer chemotherapy agent may be a taxane, e.g., paclitaxel or nab-paclitaxel.

Cancers which may be treated by the novel methods disclosed herein include cancers of female reproductive organs and tissues, and peritoneal cancer. Such cancers include, for example, ovarian, fallopian tube, uterine, cervical, vaginal, vulvar, and peritoneal cancers. In embodiments, the novel methods are directed to ovarian cancer, including platinum-resistant ovarian cancer. In embodiments, the novel methods are directed to cervical cancer. In embodiments, the novel methods are directed to uterine cancer. In embodiments, the novel methods are directed to fallopian tube cancer. In embodiments, the novel methods for treating cancers are directed to peritoneal cancer.

The new and surprising treatment methods and uses disclosed herein are believed to provide improved and effective treatments for cancer patients suffering from peritoneal cancer or cancers of female reproductive organs and tissues, including, for example, ovarian, fallopian tube, uterine, cervical, vaginal, and vulvar cancers. Results from clinical studies disclosed herein (see, e.g., Study of Relacorilant in Combination With Nab-Paclitaxel for Patients With Recurrent Platinum-Resistant Ovarian, Fallopian Tube, or Primary Peritoneal Cancer, NCT03776812) demonstrate that these methods (comprising combined administration of taxane chemotherapy and of the GR modulator relacorilant to patients suffering from female reproductive organ cancers and patients suffering from primary peritoneal cancer) provide greater benefit than taxane chemotherapy alone. For example, intermittent administration of relacorilant with nab-paclitaxel resulted in clinically meaningful benefit without increased side effect burden as compared to nab-paclitaxel monotherapy. Such benefits included improved progression free survival (PFS), with a hazard ratio (HR) of 0.66 (P=0.038; median PFS 5.6 vs 3.8 months); improved duration of response (DoR) with a HR of 0.36 (P=0.006; median DoR 5.6 vs 3.7 months); and improved overall survival (OS) with a HR of 0.67 (P=0.066; median OS 13.9 vs 12.2 months) as compared to nab-paclitaxel monotherapy alone.

As noted above, there is a large, previously unmet need for effective, well-tolerated treatments for cancers, including platinum-resistant cancers, such as ovarian cancer, cervical cancer, vaginal cancer, vulvar cancer, fallopian tube cancer, uterine cancer, and other tumors of the female reproductive organs and tissues, as well as for peritoneal cancer. The present methods and uses are believed to provide improved treatments for cancers such as peritoneal cancer and cancers of female reproductive organs and tissues.

Figures 1, 2:
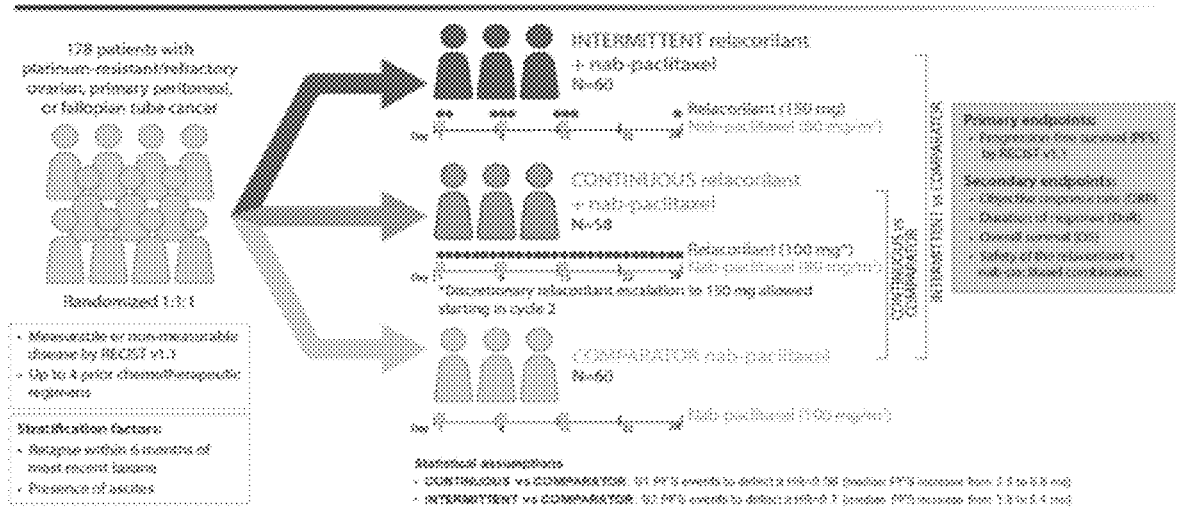
FIG. 1 is a schematic illustration of the Phase 2 clinical trial protocol of Example 1. 178 patients with platinum-resistant or platinum-refractory ovarian, primary peritoneal, or fallopian tube cancer were randomized 1:1:1 to receive either nab-paclitaxel (100 milligrams per square meter (mg/m$^2$); 60 patients; "COMPARATOR"), continuous relacorilant administration with nab-paclitaxel (80 mg/m$^2$; 58 patients; "CONTINUOUS"), or intermittent relacorilant administration with nab-paclitaxel (80 mg/m², 60 patients; "INTERMITTENT"). Patients receiving continuous relacorilant received 100 mg relacorilant per day (mg/day) (with discretionary increase in relacorilant dosage up to 150 mg/day allowed). Patients receiving intermittent relacorilant received 150 mg relacorilant on the day before, the day of, and the day after nab-paclitaxel administration. Patients were considered platinum-resistant if their disease progressed during platinum-based therapy, or if the treatment-free interval after platinum-based therapy was less than 6 months (i.e., the patient relapsed and so required further platinum-based treatment less than 6 months after a prior round of platinum-based therapy was completed). Patients were considered "platinum-refractory" if their disease progressed during or within 1 month of the last platinum-based treatment. (Platinum-refractory patients are a subgroup of platinum-resistant patients.)

FIG. 2 presents characteristics of the patients enrolled in each of the three groups of patients in the study. All but one patient had received taxane treatment prior to enrolling in the study (one patient in the "intermittent" group had not received prior taxane treatment).

Figures 3, 4A:
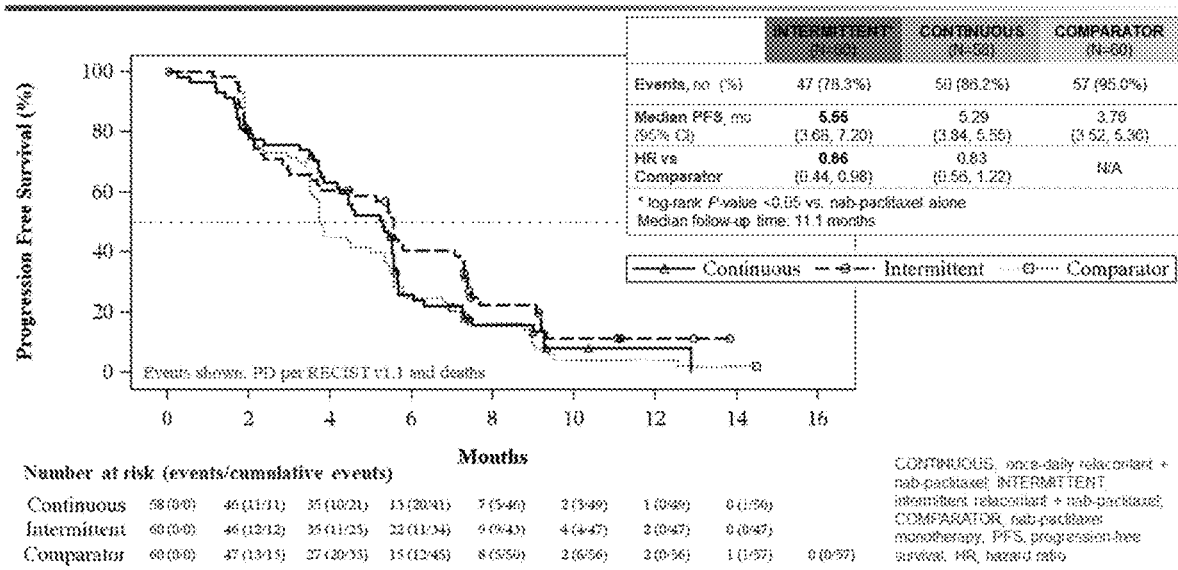

FIG. 3 presents a tabulation of the disposition of the patients by the time of the primary (interim) analysis (data as of Mar. 22, 2021).

FIG. 4A presents progression-free survival (PFS) times for the three groups of patients as of the data collected by the initial cut-off date of Mar. 22, 2021. Patients receiving nab-paclitaxel and intermittent relacorilant experienced significantly improved PFS compared to nab-paclitaxel alone (hazard ratio (HR) of 0.66, log rank test P=0.038; not adjusted for multiplicity). Their median PFS was 5.6 months, 1.8 months longer than the nab-paclitaxel monotherapy group, where it was 3.8 months. Each event is a patient experiencing disease progression (per RECIST v1.1) or death, whichever happens first. For the subgroup of patients excluding patients with primary refractory disease and excluding patients who had received more than 3 prior lines of treatment, PFS for intermittent relacorilant+nab-paclitaxel versus nab-paclitxael alone was improved with a HR 0.58, 95% CI 0.37-0.91, log-rank test P=0.0162; and a median PFS 5.6 vs 3.8 mo.

Figure 4B:
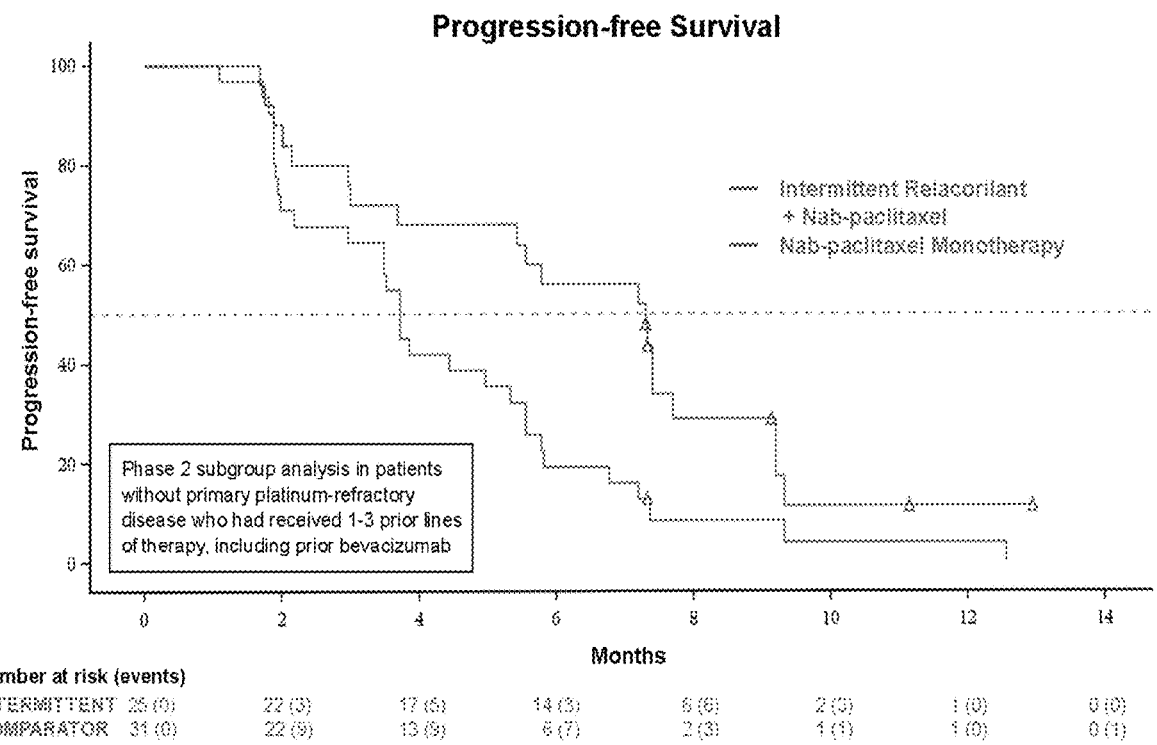

FIG. 4B presents progression-free survival (PFS) times analyzed for the subgroup of patients without primary platinum-refractory disease who had received from 1 to 3 prior lines of therapy for their cancer, which prior therapy included prior bevacizumab.

Figure 5:
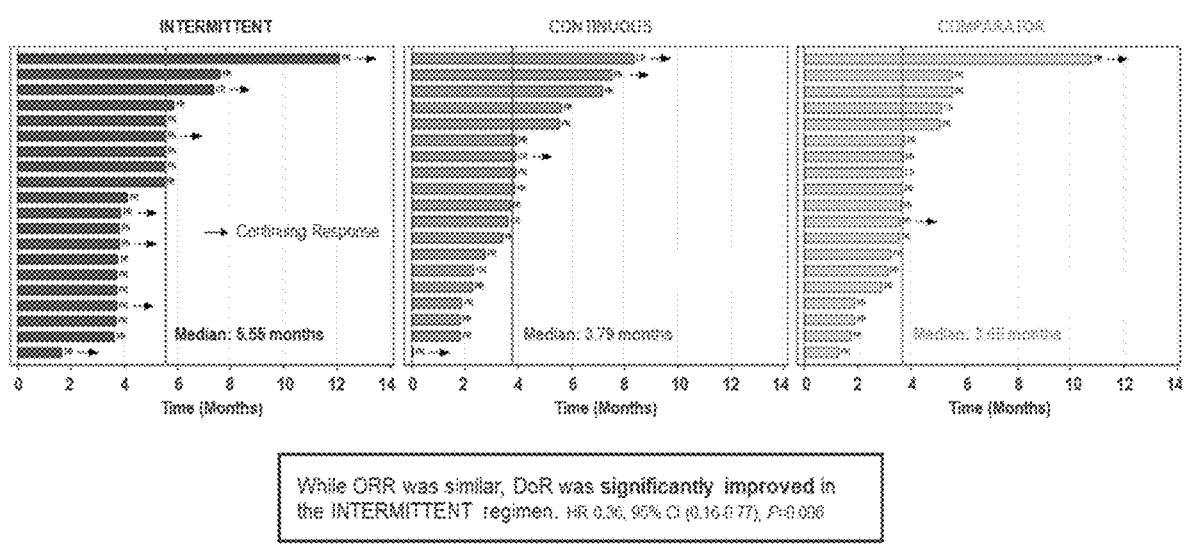

FIG. 5 illustrates the duration of response (DoR) for each of the three groups of patients as of the data collected by the initial cut-off date of Mar. 22, 2021. Duration of response was significantly improved in patients receiving intermittent relacorilant with nab-paclitaxel as compared to nab-paclitaxel alone (P=0.006; HR of 0.36), although the objective response rate (ORR) was similar for all three groups (intermittent: n=20 (35.7%); continuous: n=19 (35.2%); comparator: n=19 (35.8%)). For the subgroup excluding patients with primary refractory disease and excluding patients who had received more than 3 prior lines of treatment, DoR for intermittent relacorilant+nab-paclitaxel versus nab-paclitxael alone was improved with a HR 0.26, 95% CI 0.11-0.62, log-rank test P=0.0009; median DoR 5.6 vs 3.6 mo.

Figure 6A:
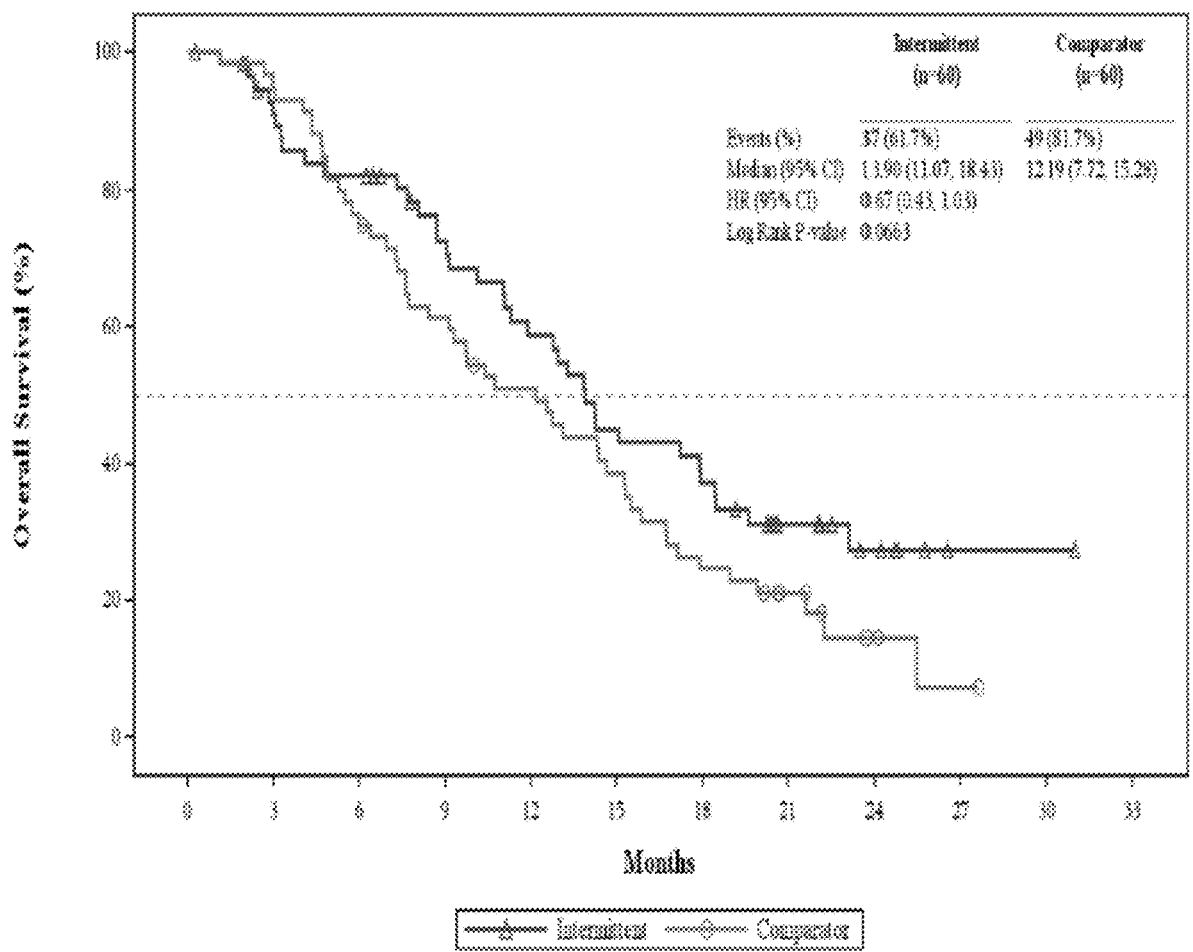

FIG. 6A illustrates overall survival (OS) time for each of the three patient groups as of the data collected by the later (pre-determined by reaching at least 120 OS events) cut-off date of Mar. 7, 2022. These data demonstrate improved OS for the group of patients receiving intermittent relacorilant along with nab-paclitaxel as compared to the group of patients receiving nab-paclitaxel alone, as indicated by the hazard ratio (HR) of 0.67 (P=0.066) for intermittent relacorilant+nab-paclitaxel, and HR of 0.85 (P=0.447) for continuous relacorilant+nab-paclitaxel compared to nab-paclitaxel only. Thus, the patients in the intermittent relacorilant arm had a 33% reduction in the risk of death as compared to the comparator group of patients. Patients receiving intermittent relacorilant had a median OS of 13.9 months, as compared to a median OS of 12.2 months for those patients who received nab-paclitaxel but did not receive relacorilant. Each event indicates the death of one patient. See also FIGS. 7B and 7C.

Figure 6B:
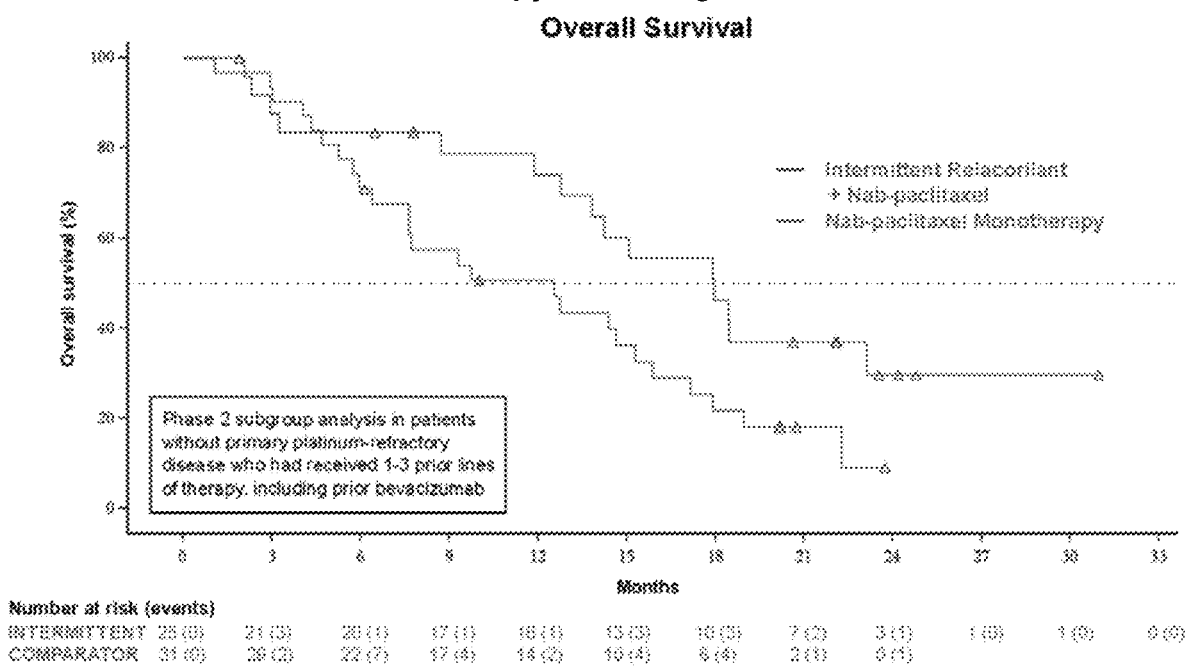

FIG. 6B illustrates overall survival (OS) times analyzed for the subgroup of patients without primary platinum-refractory disease who had received from 1 to 3 prior lines of therapy for their cancer, which prior therapy included prior bevacizumab.

FIG. 7A tabulates for comparison the progression-free survival (PFS), objective response rate (ORR), duration of response (DoR), and overall survival (OS) observed in the three groups of patients during the study. Note that this figure presents PFS, ORR, DoR, and OS data as of the earlier cut-off date of Mar. 22, 2021. Further overall survival results continued to be collected after this initial cut-off date (see FIG. 6 above and FIG. 7B). Patients who prior to the study had not responded to first-line platinum-based therapy were considered "primary platinum-refractory" patients; these patients have an especially poor prognosis. The PFS, ORR, DoR, and OS were calculated for all 178 patients in the study ("overall" columns), and also for the 167 patients who were not "primary platinum-refractory" patients ("Primary Platinum-Refractory Removed" columns). Both analyses showed that intermittent dosing of relacorilant during cycles of taxane chemotherapy administration significantly improved PFS and DoR as compared to taxane chemotherapy alone.

FIG. 7B tabulates the progression-free survival (PFS), duration of response (DoR), and overall survival (OS) data for the subgroup of patients without primary platinum-refractory disease who had received 1-3 prior lines of therapy. In this subgroup, greater improvement in PFS, DoR, and OS vs. nab-paclitaxel monotherapy was observed. The data cutoff date for the final OS analysis was Mar. 7, 2022.

Figure 7C:
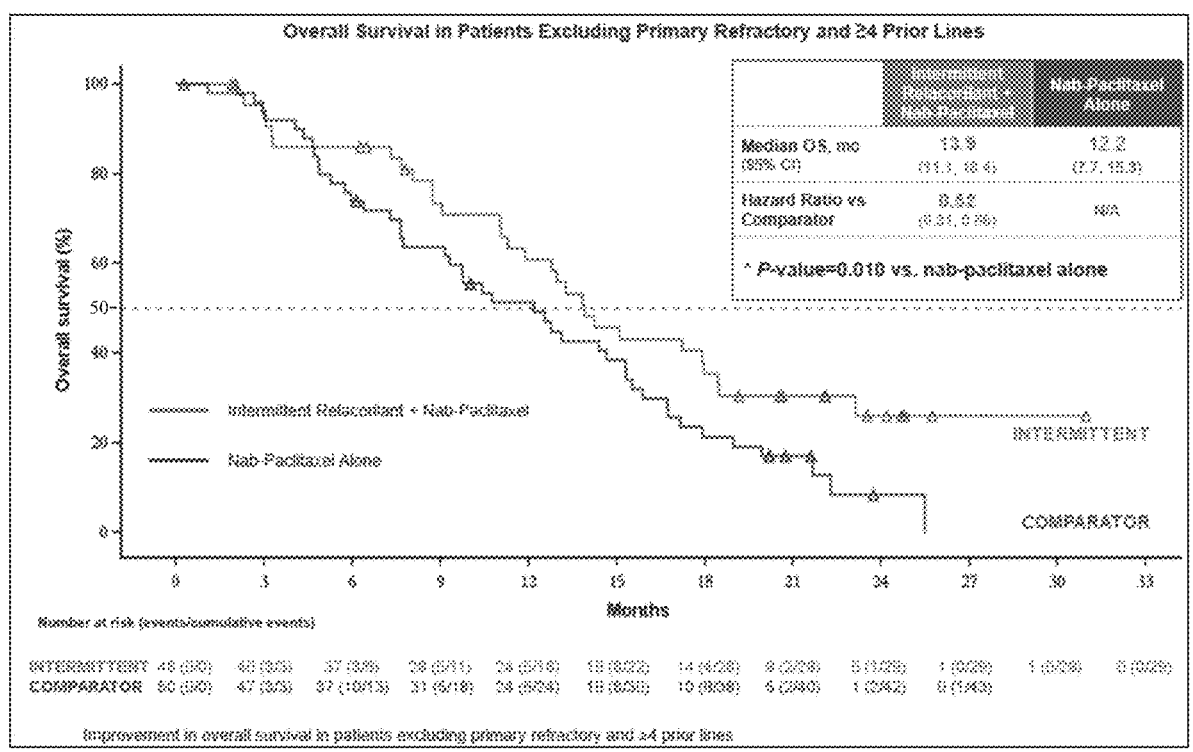

FIG. 7C illustrates the OS data up until the cut-off date of Mar. 7, 2022 in the subgroup that excluded primary platinum-refractory patients and patients that had received four or more prior lines of therapy. Excluding primary platinum-refractory patients and women who had already received four or more prior lines of therapy, women treated with relacorilant intermittently experienced a 48% reduced risk of death compared to women treated with nab-paclitaxel alone (hazard ratio: 0.52; p-value: 0.010). Their median OS was 13.9 months, compared to 12.2 months for women receiving nab-paclitaxel monotherapy.

FIG. 7D tabulates the progression-free survival (PFS), duration of response (DoR), and overall survival (OS) data for the subgroup of patients without primary platinum-refractory disease who had received 1-3 prior lines of therapy, including prior bevacizumab treatment. In this subgroup, even greater improvement in PFS, DoR, and OS was observed than that observed in the other subgroup analyses (compare, e.g., FIG. 7B, for a group in which prior bevacizumab was not required).

FIG. 8 tabulates for comparison the numbers of certain clinical conditions observed in the three groups of patients during the study. The safety and tolerability of treatment with relacorilant and nab-paclitaxel was comparable to that of treatment with nab-paclitaxel alone.

FIG. 9A presents comparisons of the levels of mRNA encoding the glucocorticoid receptor (GR) in ovarian cancer patients who received nab-paclitaxel alone as compared to those receiving relacorilant along with nab-paclitaxel. GR expression was observed in 96% of evaluable ovarian tumors in our phase 2 study. High GR expression was associated with poor response in the nab-paclitaxel-only arm. In contrast, high GR expression was associated with partial or complete response in both relacorilant+nab-paclitaxel arms (top). For patients with high GR, the rate of a partial or complete response was doubled in the relacorilant+nab-paclitaxel as compared to the nab-paclitaxel alone arm (bottom).

Figure 9B:
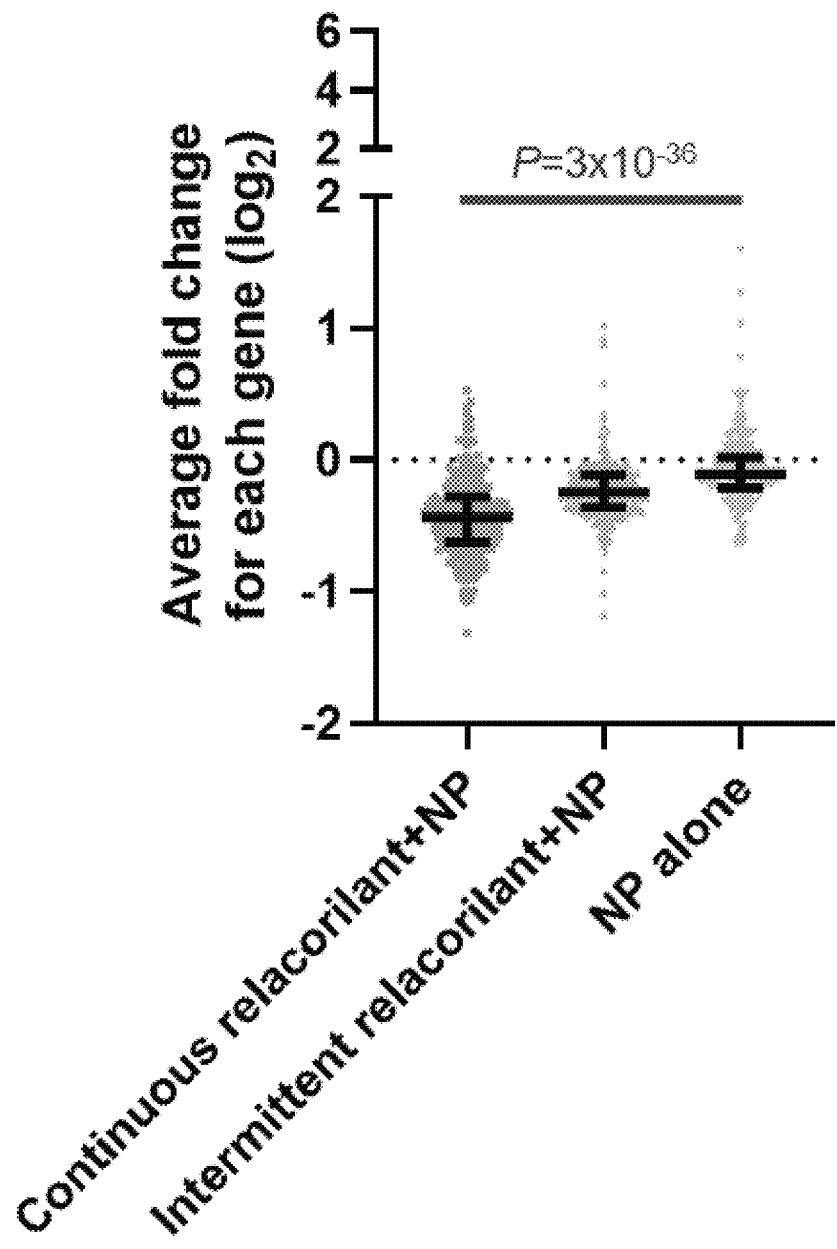

FIG. 9B shows results for "GR-inducible genes" (defined as 239 genes induced by a single dose of prednisone, as measured in whole blood from a separate healthy volunteer study). In patients receiving both relacorilant (either continuously or intermittently administered) and nab-paclitaxel (triangles), mRNA expression was suppressed in 221 of these 239 GR-inducible genes from day 1 to day 15 of cycle 1. Of 239 genes previously shown to be GR target genes, 221 were suppressed after relacorilant+nab-paclitaxel treatment. A significantly fewer number of GR target genes were suppressed by nab-paclitaxel alone (P<0.00001).

Figure 9C:
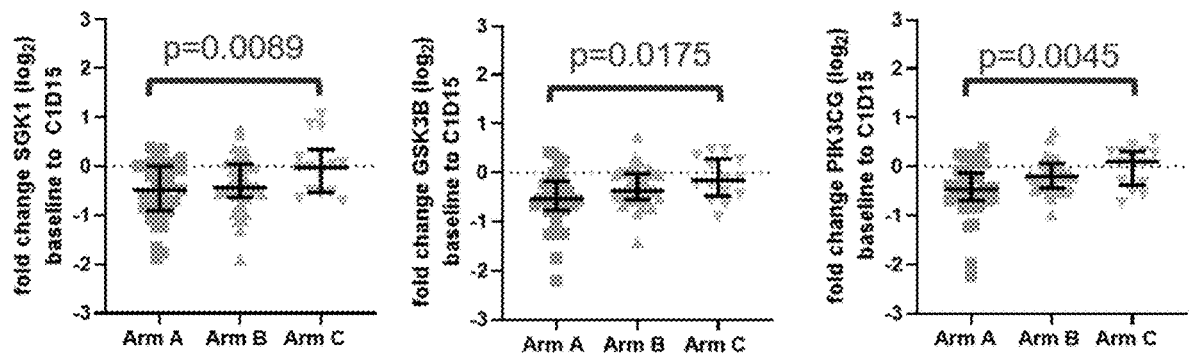

FIG. 9C shows three GR target genes that were suppressed by RELA+NP but not NP alone, including SGK1 (P=0.0089), PIK3CG (P=0.0045), and GSK3B (P=0.0175).

Figure 9D:
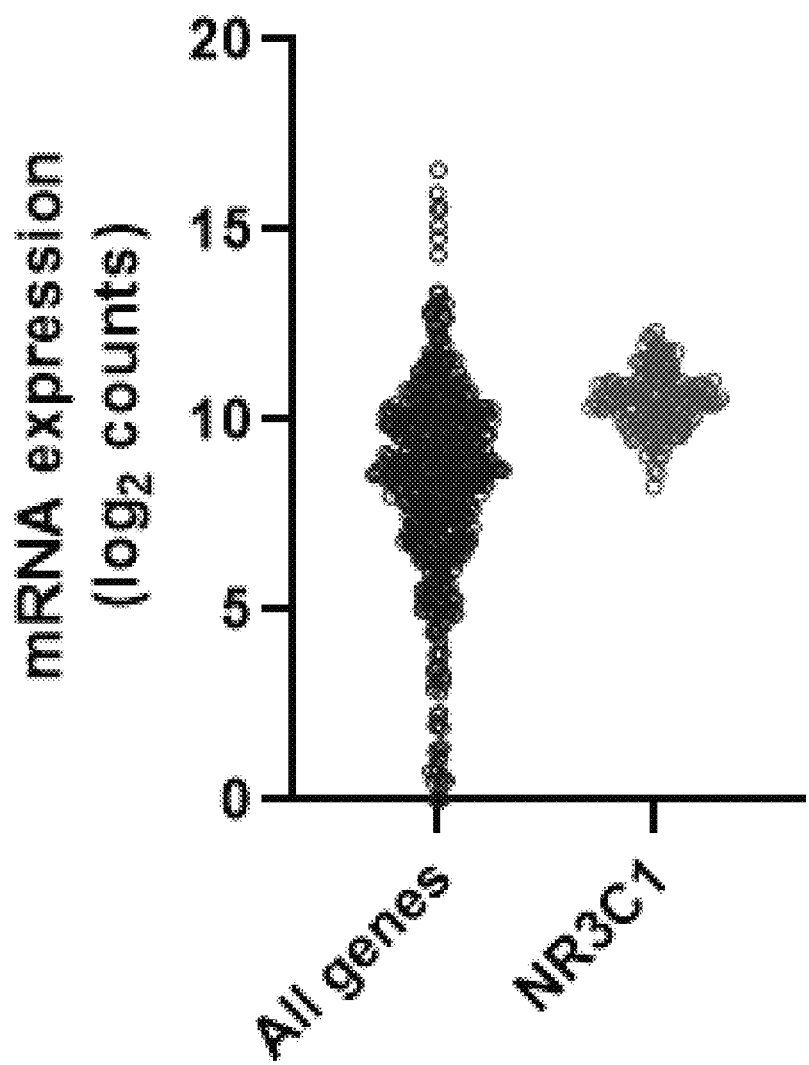

FIG. 9D presents measurements of the levels of mRNA in 137 pre-treatment tumor specimens, including tumors in patients treated with nab-paclitaxel alone and tumors in patients treated with nab-paclitaxel and relacorilant. The median for each of the 444 genes was first determined (left). NR3C1 mRNA was highly expressed in all tested tumors; the median for NR3C1 fell in the $83^{rd}$ percentile of the distribution of all genes.

Figure 10A:
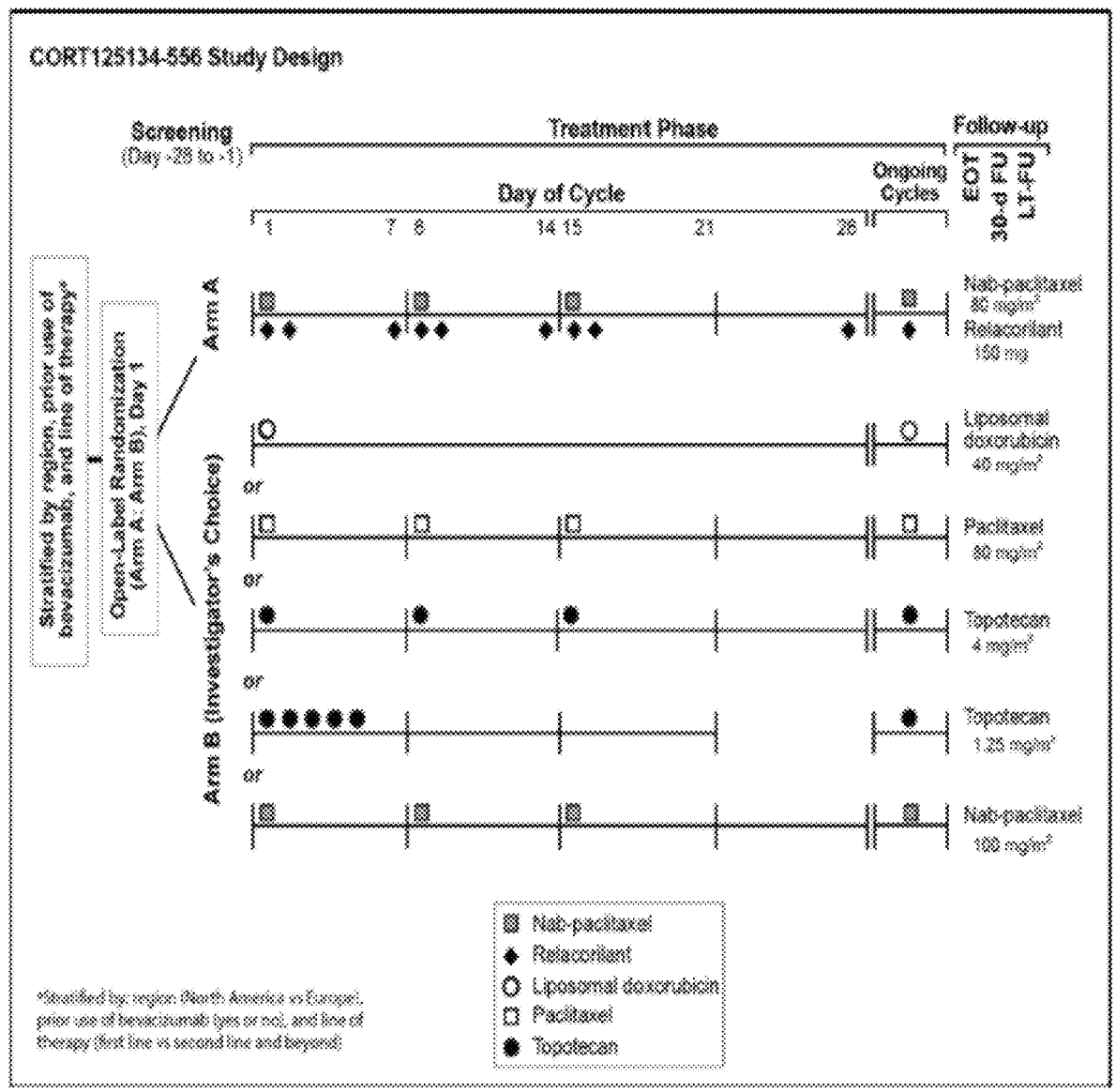

FIG. 10A is a schematic illustration of the planned clinical trial protocol of Example 2. A target enrollment of 360 patients suffering from high grade serous epithelial (Grade 3), High-grade (Grade 3) Endometrioid, and Carcinosarcoma with ≥30% endometroid epithelial tumor component, ovarian, primary peritoneal, or fallopian tube cancer, and who had Progression 6 months or less after their last dose of platinum-based therapy. Women with recurrent ovarian, primary peritoneal, or fallopian tube cancer following at least one treatment, and which is resistant to platinum-based chemotherapy, including the following histological subtypes: High-grade (Grade 3) serous epithelial ovarian, primary peritoneal, or fallopian-tube carcinoma; High-grade (Grade 3) endometrioid carcinoma; and Carcinosarcoma with a ≥30% endometroid epithelial tumor component. These criteria are expected to exclude primary-platinum refractory patients from the study. The primary endpoint to be measured will be progression free survival (PFS) by blinded independent central review (BICR) per RECIST v. 1.1. Secondary efficacy endpoints will include overall survival (OS); PFS (by investigator) per RECIST v. 1.1, best overall response (BOR); duration of response (DoR) per RECIST v. 1.1; clinical benefit rate per RECIST v. 1.1; and combined response according to RECIST v. 1.1. plus GCIG (Gynecological Cancer InterGroup) criteria. Safety endpoints will include patient safety, patient quality of life (QOL), Ca-125, pharmacodynamics, and pharmacokinetics. Patients will be randomized 1:1 to A) receive either intermittent relacorilant administration (150 mg orally) with nab-paclitaxel (80 mg/m$^2$; 180 patients), where nab-paclitaxel is administered on days 1, 8, and 15, and relacorilant is administered on days 1, 2, 7-9, 14-16, and 28 of a 28-day cycle, or B) "investigator's choice", where the patients receive, per their treating physician, either liposomal doxorubicin (40 mg/m$^2$ intravenously (i.v.)) on day 1 of a 28-day cycle; paclitaxel (80 mg/m$^2$; i.v.) on days 1, 8, 15, and 22 of a 28-day cycle; nab-paclitaxel (100 mg/m$^2$, i.v.) on days 1, 8, and 15 of a 28-day cycle; or topotecan, either 4 mg/m$^2$, i.v. on days 1, 8, and 15 of a 28-day cycle or 1.25 mg/m$^2$ i.v. on Days 1-5 of each 21-day cycle.

Figure 10B:
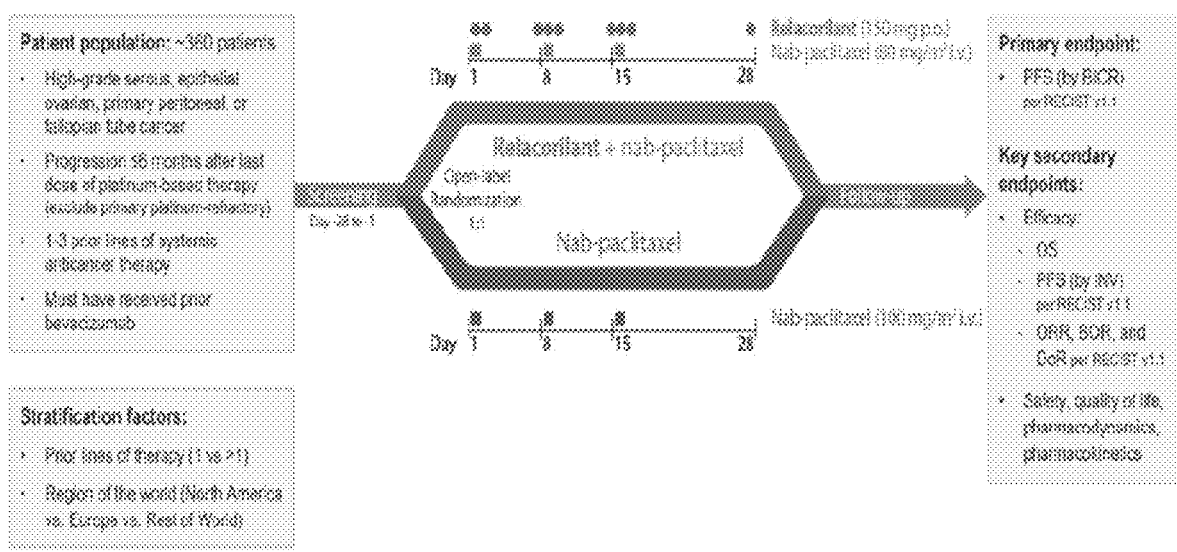

FIG. 10B is a schematic illustration of the randomized, controlled, 2-arm, open-label, multicenter phase 3 study of intermittent relacorilant+nab-paclitaxel vs. nab-paclitaxel entitled ROSELLA (NCT05257408) that has been initiated and is ongoing.

DETAILED DESCRIPTION

Applicant has surprisingly discovered that intermittent administration of a glucocorticoid receptor modulator (GRM) in combination with cancer chemotherapy provides cancer patients with greater benefit than chemotherapy alone. Intermittent GRM administration with a taxane provides greater benefit to cancer patients than taxane treatment alone. For example, Applicant has surprisingly discovered that intermittent administration of the non-steroidal GRM relacorilant, in combination with taxane chemotherapy (e.g., nab-paclitaxel) provides cancer patients with, e.g., increased duration of response and progression-free survival, than treatment with taxane alone. For example, as disclosed herein, intermittent administration of relacorilant the day before, the day of, and the day after weekly administration of nab-paclitaxel (for three successive weeks of a four-week cycle, and in multiple cycles thereof, as demonstrated in the Example herein) provides cancer patients with greater benefit than similar nab-paclitaxel treatment in the absence of relacorilant. Such greater benefit includes providing improved progression-free survival, improved duration of response, and other benefits in patients suffering from ovarian, fallopian tube, peritoneal, and other cancers.

The present surprising results differ from previous results indicating that continuous administration of relacorilant in combination with nab-paclitaxel could provide benefit. A phase 1 study of relacorilant+nab-paclitaxel demonstrated clinical activity in patients with metastatic PDAC, ovarian cancer, and other solid tumors. Combined relacorilant+nab-paclitaxel provided longer duration of benefit than prior nab-paclitaxel monotherapy, resulting in durable disease control in patients with ovarian, fallopian tube, and primary peritoneal cancer (Munster et al. 2019). Applicant discloses herein that intermittent GRM administration with taxane chemotherapy, as opposed to continuous GRM administration administration with taxane chemotherapy, surprisingly provided additional benefit as compared to no GRM.

The methods and uses disclosed herein comprise intermittent administration of an effective amount of a GRM to the subject, effective to treat cancer in the subject. In embodiments, the GRM is a selective glucocorticoid receptor modulator (SGRM). In embodiments, the methods disclosed herein comprise intermittent administration of an effective amount of a nonsteroidal GRM (where "nonsteroidal" means that the GRM does not contain a steroid structure) to the subject, effective to treat cancer in the subject.

In embodiments, the GRM is a nonsteroidal compound comprising a heteroaryl ketone fused azadecalin structure, wherein the heteroaryl ketone fused azadecalin structure is as described and disclosed in U.S. Pat. No. 8,859,774. In embodiments, the GRM is a heteroaryl ketone fused azadecalin compound disclosed in U.S. Pat. No. 8,859,774. A pharmaceutical composition for use as disclosed herein may contain a non-steroidal GRM compound comprising a heteroaryl ketone fused azadecalin structure. In embodiments, the GRM is the heteroaryl ketone fused azadecalin compound (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone ("relacorilant"), which has the following structure:

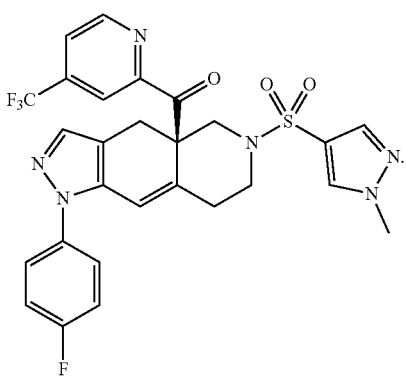

Relacorilant is disclosed in Example 18 of U.S. Pat. No. 8,859,774; it is also known as CORT125134. Relacorilant is a GRM that does not significantly affect progesterone, mineralocorticoid, androgen, or estrogen receptors. Thus, relacorilant is a SGRM, In embodiments, relacorilant is administered orally.

Intermittent administration is administration of a pharmaceutical composition at times that are more than one day apart. In embodiments, the times between administrations may be two days, several days, one week, several weeks, one month, several months, or may be longer. The times between administrations may be regular (e.g., the time between administrations is always the same number of days), or may be irregular e.g., the time between some pairs of administrations of the pharmaceutical composition is a different number of days than the time between other pairs of administrations of the pharmaceutical composition). In embodiments, the time between administrations between a first and a second administration of the pharmaceutical composition need not be the same as the time between administrations between a second and a third, or between a third and a fourth administration of the pharmaceutical composition, or between other subsequent administrations of the pharmaceutical composition.

In embodiments of the methods and uses disclosed herein, intermittent administration comprises administration of an effective amount of a GRM, such as a nonsteroidal GRM, e.g., relacorilant, on two consecutive days, waiting a period of time (an "interval"), and then again administering an effective amount of the GRM on two consecutive days; the interval may be, e.g., one week, two weeks, three weeks, four weeks, or more. The interval may be two or a few days, or may be a number of days not equal to an integer number of weeks. In embodiments of the methods disclosed herein, intermittent administration comprises administration of an effective amount of a GRM, such as a nonsteroidal GRM, e.g., relacorilant, on three consecutive days, waiting an interval, and then again administering an effective amount of the GRM on three consecutive days; the interval may be, e.g., one week, two weeks, three weeks, four weeks, or more. In embodiments of the methods disclosed herein, intermittent administration comprises administration of an effective amount of a GRM, such as a nonsteroidal GRM, e.g., relacorilant, once per week, or once every two weeks, or once per month, or twice per month, or three times per month. In embodiments of the methods disclosed herein, intermittent administration comprises administration of an effective amount of a GRM, such as a nonsteroidal GRM, e.g., relacorilant, on alternate days.

For example, the intermittent administration of the GRM, such as a heteroaryl-ketone fused azadecalin GRM, may include administration on the day that cancer chemotherapy agent is administered to the patient. The intermittent administration of the GRM, such as a heteroaryl-ketone fused azadecalin GRM, may further include administration on the day before the cancer chemotherapy agent is administered to the patient; or on the day after the cancer chemotherapy agent is administered to the patient; and may include administration of the non-steroidal GRM on the day before, the day of, and the day after the cancer chemotherapy agent is administered to the patient. The intermittent administration of the heteroaryl-ketone fused azadecalin GRM may include at least 4 days between administrations of the heteroaryl-ketone fused azadecalin GRM, in which the heteroaryl-ketone fused azadecalin GRM is not administered.

The novel methods and uses disclosed herein may be used in the treatment of a cancer patient who is also receiving cancer chemotherapy. In embodiments of the methods disclosed herein, intermittent administration of a GRM, such as a nonsteroidal GRM, e.g., relacorilant, may be timed according to the schedule of administration of a cancer chemotherapy agent to the patient. For example, the GRM may be administered on the before, or the day of, or the day after administration of a cancer chemotherapy agent to the patient. The GRM may be administered on two or more of the day before, or the day of, or the day after administration of a cancer chemotherapy agent to the patient. In embodiments of the methods and uses disclosed herein, intermittent GRM administration comprises administration of an effective amount of a GRM, such as a nonsteroidal GRM, e.g., relacorilant, on the day before, the day of, and the day after administration of a cancer chemotherapy agent to the patient. The cancer chemotherapy agent may be, e.g., a taxane such as paclitaxel or nab-paclitaxel.

In embodiments of the methods disclosed herein, intermittent administration comprises administration of an effective amount of a GRM, such as a nonsteroidal GRM, e.g., relacorilant, on the day before administration of a cancer chemotherapy agent to the patient; the cancer chemotherapy agent may be, e.g., a taxane such as paclitaxel or nab-paclitaxel. In embodiments of the methods disclosed herein, intermittent administration comprises administration of an effective amount of a GRM, such as a nonsteroidal GRM, e.g., relacorilant, on the day of administration of a cancer chemotherapy agent to the patient; the cancer chemotherapy agent may be, e.g., a taxane such as paclitaxel or nab-paclitaxel. In embodiments of the methods disclosed herein, intermittent administration comprises administration of an effective amount of a GRM, such as a nonsteroidal GRM, e.g., relacorilant, on the day after administration of a cancer chemotherapy agent to the patient; the cancer chemotherapy agent may be, e.g., a taxane such as paclitaxel or nab-paclitaxel.

The novel methods and uses disclosed herein comprising intermittent administration of a GRM, such as a non-steroidal GRM, can be used to treat a patient suffering from ovarian, fallopian tube, uterine, cervical, vaginal, vulvar, peritoneal, or other cancer. Such intermittent administration of an effective amount of a GRM, such as a non-steroidal GRM, e.g., relacorilant, in combination with cancer chemotherapy, is effective to treat the cancer. A pharmaceutical composition for use as disclosed herein may contain a non-steroidal GRM compound comprising a heteroaryl ketone fused azadecalin structure, such as, e.g., relacorilant.

The GRM, such as a non-steroidal GRM, may be orally administered. In embodiments, relacorilant is administered orally. In some cases, the GRM, such as a non-steroidal GRM, is administered by injection, infusion, or by other means.

In some cases, the effective amount of the GRM is a dose of between 1 and 100 mg/kg/day, wherein the GRM is administered with at least one chemotherapeutic agent. In some embodiments, the dose of the GRM is 1, 2, 4, 6, 8, 10, 12, 14, 16, 18, 20, 30, 40, 50 60, 70, 80, 90 or 100 mg/kg/day. In some cases, the GRM is administrated according to an intermittent administration regimen for at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, or 80 weeks.

The cancer chemotherapy agent (also termed chemotherapy agent), as used herein, may be any chemotherapy agent suitable for use in treating the cancer, e.g., any chemotherapy agent suitable for use in treating from ovarian, fallopian tube, uterine, cervical, vaginal, vulvar, or peritoneal cancer. The cancer chemotherapy agent may be, e.g., a chemotoxic compound, an antiproliferative agent, an anti-metastatic agent, and may be an antibody, or other agent or treatments that can inhibit, stop, or reverse the growth or spread of cancer, alone or in conjunction with other agents. In embodiments of the methods and uses disclosed herein, the cancer chemotherapy agent may be a taxane. The taxane may be, e.g., paclitaxel, nab-paclitaxel, docetaxel, larotaxel, tesetaxel, cabazitaxel, or ortataxel. In embodiments, the cancer chemotherapy agent is a taxane containing paclitaxel, e.g., nab-paclitaxel.

Accordingly, Applicant discloses herein a method of treating cancer, the method comprising: Intermittently administering an effective amount of a GRM to a patient hosting a cancer, wherein said patient is in need of, and is receiving, cancer chemotherapy treatment for said cancer, said treatment comprising administration of a cancer chemotherapy agent according to a cancer chemotherapy dosing schedule, said dosing schedule requiring that there be at least one day without administration of said cancer chemotherapy agent between days on which the cancer chemotherapy agent is administered to the patient, wherein said intermittent administration comprises administration of said GRM on the same day that said cancer chemotherapy agent is administered to the patient, thereby treating said cancer. In embodiments, the GRM is a non-steroidal GRM, such as a heteroaryl-ketone fused azadecalin GRM, e.g., relacorilant.

In embodiments of the methods disclosed herein, the GRM is also administered on the day after the cancer chemotherapy agent is administered to the patient. In embodiments of the methods disclosed herein, the GRM is also administered on the day before the cancer chemotherapy agent is administered to the patient. In embodiments of the methods disclosed herein, the GRM is administered on the day before, the day of, and the day after the cancer chemotherapy agent is administered to the patient. In embodiments, the GRM is a non-steroidal GRM, such as a heteroaryl-ketone fused azadecalin GRM, e.g., relacorilant.

Applicant also discloses herein the use of a GRM, such as a non-steroidal GRM such as a heteroaryl-ketone fused azadecalin GRM (e.g., relacorilant) in any of the methods disclosed herein for treating cancer. The uses include the use of such a GRM in the manufacture of a medicament for treating a cancer according to a method disclosed herein. In embodiments of the methods and uses disclosed herein, the cancer chemotherapy dosing schedule comprises administration of said cancer chemotherapy agent on a first day, and again on a subsequent day that follows said first day after an interval of at least one day (i.e., is not the next day after said first day), without administration of said cancer chemotherapy agent on the day or days between the first day and said subsequent day. For example, in embodiments of the methods and uses disclosed herein, the cancer chemotherapy dosing schedule comprises administration of said cancer chemotherapy agent on a first day, and again on a day seven days after said first day, without administration of said cancer chemotherapy agent on days between the first and said day seven days after said first day.

In further embodiments of the methods disclosed herein, the cancer chemotherapy agent is administered to the patient according to the cancer chemotherapy dosing schedule for three consecutive weeks. In yet further embodiments of the methods disclosed herein, the cancer chemotherapy agent is administered to the patient according to the cancer chemotherapy dosing schedule for three consecutive weeks, and then not administered the week following said three consecutive weeks. In embodiments, the cancer chemotherapy agent is administered to the patient according to the cancer chemotherapy dosing schedule for three consecutive weeks, and then not administered the week following the last of said three consecutive weeks, and then said weekly dosing regimen is repeated for three further consecutive weeks.

Applicant further discloses uses of a pharmaceutical composition for treating cancer, wherein said cancer treatment comprises intermittently administering an effective amount of a GRM, such as a heteroaryl-ketone fused azadecalin GRM to a patient hosting a cancer, wherein said patient is in need of, and is receiving, cancer chemotherapy treatment for said cancer, said treatment comprising administration of a cancer chemotherapy agent according to a cancer chemotherapy dosing schedule, said dosing schedule requiring that there be at least one day without administration of said cancer chemotherapy agent between days on which the cancer chemotherapy agent is administered to the patient, wherein said intermittent administration comprises administration of said GRM on the same day that said cancer chemotherapy agent is administered to the patient, said pharmaceutical composition comprising a pharmaceutically acceptable excipient and a GRM such as a heteroaryl-ketone fused azadecalin GRM, e.g., relacorilant.

In embodiments of the uses disclosed herein, the cancer to be treated may be, e.g., ovarian, fallopian tube, uterine, cervical, vaginal, vulvar, or peritoneal cancer. In embodiments, the cancer is ovarian cancer. In embodiments, the cancer is fallopian tube, uterine, cervical, vaginal, vulvar, or peritoneal cancer. In embodiments, the cancer is platinum-resistant ovarian cancer. In embodiments, the cancer is platinum-resistant fallopian tube, uterine, cervical, vaginal, vulvar, or peritoneal cancer. In embodiments of the uses disclosed herein, the cancer chemotherapy agent may be a taxane. In embodiments of the uses, the taxane may be, e.g., paclitaxel, nab-paclitaxel, docetaxel, larotaxel, tesetaxel, cabazitaxel, or ortataxel. In embodiments, the cancer chemotherapy agent is a taxane containing paclitaxel, e.g., nab-paclitaxel.

In embodiments of the uses disclosed herein, the GRM (such as a non-steroidal GRM, e.g., a heteroaryl-ketone fused azadecalin GRM) is also administered on the day after the cancer chemotherapy agent is administered to the patient. In embodiments of the uses disclosed herein, the heteroaryl-ketone fused azadecalin GRM is also administered on the day before the cancer chemotherapy agent is administered to the patient. In embodiments of the uses disclosed herein, the heteroaryl-ketone fused azadecalin GRM is administered on the day before, the day of, and the day after the cancer chemotherapy agent is administered to the patient.

In embodiments of the uses disclosed herein, the cancer chemotherapy dosing schedule comprises administration of said cancer chemotherapy agent on a first day, and again on a day seven days after said first day, without administration of said cancer chemotherapy agent on days between the first and said day seven days after said first day.

In further embodiments of the uses disclosed herein, the cancer chemotherapy agent is administered to the patient according to the cancer chemotherapy dosing schedule for three consecutive weeks. In yet further embodiments of the uses disclosed herein, the cancer chemotherapy agent is administered to the patient according to the cancer chemotherapy dosing schedule for three consecutive weeks, and then not administered the week following the last of said three consecutive weeks. In embodiments of the uses disclosed herein, the cancer chemotherapy agent is administered to the patient according to the cancer chemotherapy dosing schedule for three consecutive weeks, and then not administered the week following the last of said three consecutive weeks, and then said weekly dosing regimen is repeated for three further consecutive weeks.

B. Definitions

As used herein, the term "tumor" and the term "cancer" are used interchangeably and both refer to an abnormal growth of tissue that results from excessive cell division. A "malignant" tumor may invade surrounding tissue (such tumor invasion is termed "locally advanced"). A malignant tumor that leaves the organ of origin is one that has metastasized.

As used herein, the term "first-line" refers to that therapy which is first administered to a patient upon diagnosis (e.g., of a cancer). Other often used terms for "first-line" therapies include induction therapy, primary therapy, and primary treatment.

As used herein, the terms "overall survival" and "overall survival rate" (OS) refer to the numbers or percentage of patients in a treatment group who are still alive for a certain period, or at a selected time-point, after the start of treatment.

As used herein, the term "progression-free survival" ("PFS") refers to the length of time during and after initiation of treatment during which the cancer does not get worse (does not "progress", e.g., a tumor does not significantly grow in size, or does not metastasize). Progression-free survival is an indication of how well a treatment works.

As used herein, the terms "response" and "response rate" refer to an improvement related to treatment, or slowing or cessation of disease progression. For example, a patient who exhibits improvement during or following treatment, such as reduction in severity of symptoms, slowing or cessation of tumor growth, improvement in quality of life, or other improvement, is said to respond to treatment.

As used herein, the terms "objective response" and "objective response rate" (ORR) refer to a measurable response, i.e., a measurable improvement related to treatment. ORR is defined as the proportion of patients with tumor size reduction of a predefined amount and for a minimum time period; see Response Evaluation Criteria in Solid Tumors ("RECIST") guidelines version 1.1 (available via the World Wide Web at the URL: ctep.cancer.gov/protocolDevelopment/docs/recist_guideline.pdf).

As used herein, the term "duration of response" (DoR) refers to the length of time that a patient experiences an improvement related to treatment.

As used herein, the terms "partial response" and "partial remission" (PR) refer to an at least a 30% decrease in the sum of the diameters (SOD) of target lesions, taking as reference the baseline SOD in response to treatment.

As used herein, the terms "complete response" and "complete remission" (CR) refer to a disappearance of all signs of cancer in response to treatment—no detectable evidence of tumor. CR is generally measured through imaging studies (e.g., CT scans) or through histopathologic assessment (e.g., bone marrow biopsy or breast cancer resection specimens).

As used herein, the term "relapse" refers to a return of cancer, or to a reappearance or increase of cancer symptoms following a period of response to treatment.

As used herein, the term "platinum-resistant" refers to a cancer, after a successful treatment (e.g., a partial or complete response) with platinum-containing chemotherapy (e.g., cisplatin or carboplatin), that relapses or progresses within a certain period of time after treatment. For example, ovarian cancer that comes back within 6 months after platinum-containing chemotherapy treatment is considered platinum-resistant.

As used herein, the term "platinum-refractory" refers to a cancer that does not respond to treatment with anticancer drugs that contain the metal platinum, such as cisplatin and carboplatin. Disease progressing or relapsing immediately following upfront platinum-based therapy is indicative of not responding to treatment. A "primary platinum-refractory" patient does not respond to the first treatment with platinum-based cancer therapy; other patients may initially respond to platinum-based cancer therapy, but, upon recurrence of the cancer, fail to respond to further platinum-based cancer therapy. Platinum-refractory patients are a subgroup of platinum-resistant patients.)

As used herein, the term "hazard ratio" (HR) refers to a measure of patient response (e.g., survival) at any point in time in a group of patients who have been given a specific treatment compared to patient response (e.g., survival) in a control group given another treatment or a placebo. Patient survival may be measured, e.g., as progression-free survival, overall survival, or other survival measure. A hazard ratio of one means that there is no difference in survival between the two groups. A hazard ratio of greater than one or less than one means that survival was better in one of the groups. For example, where HR is calculated as overall survival in the experimental compared to overall survival in the control arm, a HR<1 indicates longer overall survival in the experimental arm. More generally, a hazard ratio refers to a measure of how often a particular event happens in one group compared to how often it happens in another group, over time.

As used herein, the term "ascites" refers to abnormal fluid build-up, typically in the abdomen.

As used herein, the terms "cancer chemotherapeutic", "cancer chemotherapeutic agent", "cancer therapeutic", "cancer chemotherapy agent", and "chemotherapy agent"

refer to any and all anti-neoplastic agents, compounds, and compositions used to treat cancer. In addition to chemotoxic compounds and formulations that are typically toxic to cancer cells (and often non-cancerous cells as well), as used herein, cancer chemotherapeutic agents and treatments by such agents may also include antibody treatments, toxic or antibiotic compounds and formulations that are typically toxic to cancer cells (and often non-cancerous cells as well), antiproliferative agents (reducing cancer cell growth or replication), agents that are anti-metastatic (reducing metastases), and other agents and treatments that inhibit, stop, or reverse the growth or spread of cancer in a cancer patient. Cancer chemotherapy agents may be used alone, or in combination with other cancer chemotherapy or other agents.

Cancer chemotherapeutic agents include, but are not limited to, doxorubicin, vincristine, cyclophosphamide, fluorouracil (e.g., 5-fluorouracil (5-FU)), topotecan, interferons, platinum derivatives, taxanes (e.g., paclitaxel, nab-paclitaxel, docetaxel, larotaxel, tesetaxel, cabazitaxel, and ortataxel), vinca alkaloids (e.g., vinblastine), anthracyclines (e.g., doxorubicin), epipodophyllotoxins (e.g., etoposide), cisplatin, methotrexate, actinomycin D, dolastatin 10, trimetrexate, metoprine, daunorubicin, teniposide, alkylating agents (e.g., chlorambucil), 5-fluorouracil, camptothecin, and cisplatin, and anti-inflammatory agents such as, e.g., colchicine, among others.

As used herein, the term "taxane" refers to a class of diterpene compounds having a taxadiene core. Many taxanes are useful as cancer chemotherapeutic drugs, typically acting as mitotic inhibitors and antimicrotubule agents. Taxanes include paclitaxel (e.g., TAXOL (paclitaxel; Bristol-Myers Squibb Oncology, Princeton, N.J.)), nab-paclitaxel (ABRAXANE®, "Abx"; albumin-engineered nanoparticle formulations of paclitaxel also known as nab-paclitaxel (American Pharmaceutical Partners, Schaumberg, Ill.)), TAXOTERE® (docetaxel, doxetaxel; Sanofi-Aventis), larotaxel, tesetaxel, cabazitaxel, and ortataxel.

As used herein, the term "bevacizumab" refers to an antibody drug that binds to the protein vascular endothelial growth factor (VEGF). Bevacizumab is used, alone or with other drugs, to treat a variety of cancer types, including, e.g., ovarian, cervical, colorectal, lung, and other cancers. It is believed that bevacizumab treats cancer by inhibiting the growth of new blood vessels. Bevacizumab is commercially available under brand names including Avastin, Mvasi, and Zirabev.

As used herein, the terms "PARP inhibitor" and "poly (ADP-ribose) polymerase inhibitor" refer to substances that inhibit or block the enzyme poly (ADP-ribose) polymerase (PARP). PARP inhibitors may be used in combination with other cancer chemotherapy agents. PARP is believed to be an important cellular tool in repairing DNA damage; one aim of many cancer chemotherapy agents is to damage the DNA of cancerous cells. It is believed that PARP inhibitors treat cancer by inhibiting DNA repair in cancer cells treated with cancer chemotherapy agents.

As used herein, the terms "adverse event" and "adverse effect" refer to unexpected medical problems experienced by patients during treatment with a drug or other therapy, including during treatment by an experimental treatment, e.g., in a clinical trial. Adverse events may be mild, moderate, or severe, and may be caused by something other than the drug or therapy being given. Adverse events which may be observed in cancer patients include, for example, neutropenia, anemia, neuropathy (such as peripheral neuropathy), fatigue, swelling, ascites, nausea, vomiting, and other events or symptoms.

As used herein, the terms "safe" and "safety" with regard to a clinical trial refer to the risk of, or amount of, or numbers of adverse events in a clinical trial, typically a clinical trial which compares the effects of a test treatment to the effects of a standard treatment. A new drug, new treatment, or new treatment method, that results in fewer or similar numbers of adverse events, or similar severity of observed adverse events, associated with the patients receiving the test treatment as compared to the standard treatment, would be judged "safe" (where similar means that the numbers of adverse events are not significantly greater than the numbers of adverse events associated with the standard treatment).

As used herein, the terms "patient" and "subject" refer to a human who is or will be receiving, or has received, treatment for a disease or condition.

As used herein, the term "effective amount" or "therapeutic amount" refers to an amount of a pharmacological agent effective to treat, eliminate, or mitigate at least one symptom of the disease being treated. In some cases, "therapeutically effective amount" or "effective amount" can refer to an amount of a functional agent or of a pharmaceutical composition useful for exhibiting a detectable therapeutic or inhibitory effect. The effect can be detected by any assay method known in the art. An effective amount can be an amount effective to evoke an antitumor response. For the purpose of this disclosure, the effective amount of GRM or the effective amount of a chemotherapeutic agent is an amount that would bring about a desired beneficial clinical outcome related to cancer improvement when combined with a chemotherapeutic agent or GRM, respectively. Such a desired beneficial clinical outcome may be, e.g., a slowing or cessation in tumor growth; a reduction in tumor size or tumor load; an improvement in a symptom or co-morbidity, or lessening in numbers of adverse events, such as, e.g., a lessening of neutropenia, anemia, neuropathy, or fatigue; an improvement in quality of life; or other improvement.

As used herein, the terms "administer," "administering," "administered" or "administration" refer to providing a compound or a composition (e.g., one described herein), to a subject or patient. Administration may be by oral administration (i.e., the subject receives the compound or composition via the mouth, as a pill, capsule, liquid, or in other form suitable for administration via the mouth. Oral administration may be buccal (where the compound or composition is held in the mouth, e.g., under the tongue, and absorbed there). Administration may be by injection, i.e., delivery of the compound or composition via a needle, microneedle, pressure injector, or other means of puncturing the skin or forcefully passing the compound or composition through the skin of the subject. Injection may be intravenous (i.e., into a vein); intraarterial (i.e., into an artery); intraperitoneal (i.e., into the peritoneum); intramuscular (i.e., into a muscle); or by other route of injection. Routes of administration may also include rectal, vaginal, transdermal, via the lungs (e.g., by inhalation), subcutaneous (e.g., by injection, or by absorption into the skin from an implant containing the compound or composition), or by other route.

The terms "measuring", "measuring levels", "measuring the level," and the like, refer determining, detecting, or quantitating the amount, level, or concentration of the target analyte A target analyte may be, for example, an mRNA, or a hormone (e.g., cortisol or ACTH), or other target analyte in a sample obtained from a subject. The sample may be, e.g., a blood sample. A level may be measured from a fraction of a sample. For example, an analyte level may be measured in the plasma fraction of a blood sample; may be measured in a serum fraction of a blood sample; or, in embodiments, may be measured in whole blood.

As used herein, the term "sample" refers to a biological sample obtained from a human subject. Such samples are typically removed from the subject, and, when obtained, become entirely separate from the subject (i.e., are in vitro samples). The sample can be any cell, tissue or fluid sample obtained from a human subject. The sample may be, e.g., a blood sample, a saliva sample, a urine sample, or other sample obtained from the patient. Samples can be subject to various treatment, storage or processing procedures before being analyzed according to the methods described herein. Generally, the terms "sample" or "samples" are not intended to be limited by their source, origin, manner of procurement, treatment, processing, storage or analysis, or any modification. Thus, in embodiments, samples are in vitro samples and may be analyzed using in vitro methods. The methods disclosed herein are in vitro methods when used with samples obtained from, and removed from, the human subject.

As used herein, the term "AUC" means the area under the concentration-time curve, and serves as a measure of the levels of a drug in a subject to whom the drug has been administered. Drug levels may be measured in samples obtained from a patient, such as whole blood, plasma, or serum samples; urine samples; saliva samples; or other samples.

As used herein, the term "$C_{max}$" means the maximum observed concentration of a drug in a subject, or in a sample obtained from a subject, to whom the drug has been administered. $C_{max}$ may be measured, for example, in whole blood, plasma, or serum samples; urine samples; saliva samples; or in other samples.

As used herein, the term "exposure" refers to the amount of a drug available systemically that can result in activity following administration of the drug to a patient. Drug exposure may not be identical to dose since not all of a drug administered to a patient may be available for clinical effect (e.g., some drug may be excreted, or metabolized, or otherwise unavailable). Exposure may be measured by AUC or by $C_{max}$, both of which provide objective measures of the drug in the patient.

As used herein, the term "combination therapy" refers to the administration of at least two pharmaceutical agents to a patient to treat a disease. The two agents may be administered simultaneously, or sequentially in any order during the entire or portions of the treatment period. The at least two agents may be administered following the same or different dosing regimens. In some cases, one agent is administered following a scheduled regimen while the other agent is administered intermittently. In some cases, both agents are administered intermittently.

As used herein, the terms "co-administration", "concomitant administration", "combined administration", "combination treatment", and the like refer to the administration of at least two pharmaceutical agents to a subject to treat a disease or condition. The two agents may be administered simultaneously, or sequentially in any order during the entire or portions of the treatment period. The at least two agents may be administered following the same or different dosing regimens. Such agents may include, for example, e.g., relacorilant and another drug, which may be, e.g., a drug useful in treating cancer, or another therapeutic agent. In some cases, one agent is administered intermittently. In some cases, both agents are administered intermittently. In some cases, a first pharmaceutical agent may be administered once per week for one, two, or three weeks and a second pharmaceutical may be administered on one or more of the day before, the day of, and the day after administration of the first pharmaceutical agent.

As used herein, the term "compound" is used to denote a molecular moiety of unique, identifiable chemical structure. A molecular moiety ("compound") may exist in a free species form, in which it is not associated with other molecules. A compound may also exist as part of a larger aggregate, in which it is associated with other molecule(s), but nevertheless retains its chemical identity. A solvate, in which the molecular moiety of defined chemical structure ("compound") is associated with a molecule(s) of a solvent, is an example of such an associated form. A hydrate is a solvate in which the associated solvent is water. The recitation of a "compound" refers to the molecular moiety itself (of the recited structure), regardless of whether it exists in a free form or an associated form.

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As used herein, the terms "steroid" and "steroids", and the phrase "steroidal backbone" refer to compounds that contain a steroidal backbone containing seventeen carbon atoms, bonded in four fused rings, the structure of which is:

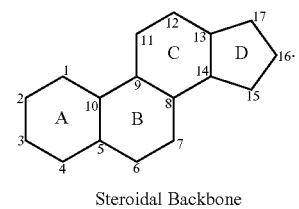

Formula 1

Steroidal Backbone

Cortisol contains a steroidal backbone, is a steroid compound, and is a steroid hormone.

As used herein, the phrase "non-steroidal backbone" in the context of GRMs refers to GRMs that do not share structural homology to, or are not modifications of, cortisol or other compounds containing a steroid backbone. Non-steroidal compounds lack the steroidal backbone.

As used herein, the term "glucocorticoid" ("GC") includes any compound known in the art that binds to and activates a glucocorticoid receptor. A GC is thus a glucocorticoid receptor agonist; other terms for GC include corticoid, corticosteroid, steroid, and glucocorticosteroid. "Glucocorticosteroid" refers to a steroid hormone or steroidal molecule that binds to the glucocorticoid receptor. In humans and many other mammals, the primary GC is cortisol; however, in rodents, for example, corticosterone plays that role. Other GCs include, for example, dexamethasone, prednisone, prednisolone, triamcinolone, hydrocortisone, beclamethasone, and other natural and synthetic compounds. Glucocorticosteroids are typically characterized by having 21 carbon atoms, an α,β-unsaturated ketone in ring A, and an α-ketol group attached to ring D. They differ in the extent of oxygenation or hydroxylation at C-11, C-17 and C-19 (Rawn, "Biosynthesis and Transport of Membrane Lipids and Formation of Cholesterol Derivatives," in Biochemistry, Daisy et al. (eds.), 1989, pg. 567).

As used herein, the term "glucocorticoid receptor" ("GR") refers to the type II GR, a family of intracellular receptors which specifically bind to cortisol and/or cortisol analogs such as dexamethasone (See, e.g., Turner & Muller, J. Mol. Endocrinol. Oct. 1, 2005 35 283-292). The glucocorticoid receptor is also referred to as the cortisol receptor. The term includes isoforms of GR, recombinant GR and mutated GR. The gene encoding GR is termed NR3C1.

The term "glucocorticoid receptor modulator" (GRM) refers to any compound which modulates GC binding to GR. For example, a GRM that acts as an agonist, such as dexamethasone, increases the activity of tyrosine aminotransferase (TAT) in HepG2 cells (a human liver hepatocellular carcinoma cell line; ECACC, UK). A GRM that acts as an antagonist, such as mifepristone, decreases the activity of tyrosine aminotransferase (TAT) in HepG2 cells. TAT activity can be measured as outlined in the literature by A. Ali et al., J. Med. Chem., 2004, 47, 2441-2452.

As used herein, the term "selective glucocorticoid receptor modulator" (SGRM) refers to any composition or compound which modulates GC binding to GR, or modulates any biological response associated with the binding of a GR to an agonist. By "selective," the drug preferentially binds to the GR rather than other nuclear receptors, such as the progesterone receptor (PRO), the mineralocorticoid receptor (MR) or the androgen receptor (AR). It is preferred that the selective glucocorticoid receptor modulator bind GR with an affinity that is 10× greater (1/10$^{th}$ the K$_d$ value) than its affinity to the MR, AR, or PRO. Relacorilant is a SGRM.

"Glucocorticoid receptor antagonist" (GRA) refers to any compound which inhibits GC binding to GR. Accordingly, GR antagonists can be identified by measuring the ability of a compound to inhibit the binding of dexamethasone to GR. TAT activity can be measured as outlined in the literature by A. Ali et al., J. Med. Chem., 2004, 47, 2441-2452. A GRA is a compound with an IC$_{50}$ (half maximal inhibition concentration) of less than 10 micromolar. See Example 1 of U.S. Pat. No. 8,859,774, the entire contents of which is hereby incorporated by reference in its entirety. A GRA is a GRM.

Compounds comprising a heteroaryl-ketone fused azadecalin structure (which may also be termed a heteroaryl-ketone fused azadecalin backbone) may be nonsteroidal compounds, may be GRM compounds, and may be SGRM compounds. Exemplary heteroaryl-ketone fused azadecalin compounds are described in U.S. Pat. No. 8,859,774. In embodiments, a heteroaryl-ketone fused azadecalin GRM for use in the methods and uses disclosed herein is the compound (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone (Example 18 of U.S. Pat. No. 8,859,774), also known as "relacorilant" and as "CORT125134", which has the following structure:

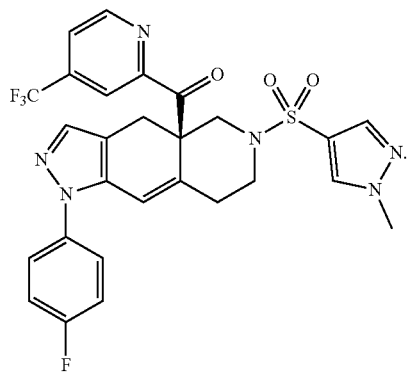 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

As used herein, the term "composition" is intended to encompass a product comprising the specified ingredients such as the said compounds, their tautomeric forms, their derivatives, their analogues, their stereoisomers, their polymorphs, their deuterated species, their pharmaceutically acceptable salts, esters, ethers, metabolites, mixtures of isomers, their pharmaceutically acceptable solvates and pharmaceutically acceptable compositions in specified amounts, as well as any product which results, directly or indirectly, from combination of the specified ingredients in the specified amounts. Such term in relation to a pharmaceutical composition is intended to encompass a product comprising the active ingredient (s), and the inert ingredient (s) that make up the carrier, as well as any product which results, directly or indirectly, in combination, complexation or aggregation of any two or more of the ingredients, or from dissociation of one or more of the ingredients, or from other types of reactions or interactions of one or more of the ingredients. Accordingly, the pharmaceutical compositions of the present invention are meant to encompass any composition made by admixing compounds of the present invention and their pharmaceutically acceptable carriers.

In some embodiments, the term "consisting essentially of" refers to a composition in a formulation whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" can refer to compositions which contain the active ingredient and components which facilitate the release of the active ingredient. For example, the composition can contain one or more components that provide extended release of the active ingredient over time to the subject. In some embodiments, the term "consisting" refers to a composition, which contains the active ingredient and a pharmaceutically acceptable carrier or excipient.

"Pharmaceutically-acceptable excipient" and "pharmaceutically-acceptable carrier" refer to a substance that aids the administration of an active agent to—and absorption by—a subject and can be included in the compositions of the present invention without causing a significant adverse toxicological effect on the patient. As used herein, these terms are intended to include any and all solvents, dispersion media, coatings, antibacterial and antifungal agents, antioxidant agents, isotonic and absorption delaying agents, and the like, compatible with pharmaceutical administration. Non-limiting examples of pharmaceutically-acceptable excipients include water, NaCl, normal saline solutions, lactated Ringer's, normal sucrose, normal glucose, binders, fillers, disintegrants, encapsulating agents, plasticizers, lubricants, coatings, sweeteners, flavors and colors, and the like. One of ordinary skill in the art will recognize that other pharmaceutical excipients are useful in the present invention. The use of such media and agents for pharmaceutically active substances is well known in the art. Except insofar as any conventional media or agent is incompatible with the active compound, use thereof in the compositions is contemplated. Supplementary active compounds can also be incorporated into the compositions. One of ordinary skill in the art will recognize that other pharmaceutical excipients are useful in the present invention.

Methods for the identification or characterization of GRM compounds are known in the art. A GRM binds to GR and modulates the activity of the GR. For example, a GRM may antagonize GR activity by inhibiting GR binding of other agents which activate GR; such modulation may be detected by observation of GR-mediated activity. Compounds that have demonstrated the desired binding affinity to GR may be tested for their activity in inhibiting GR-mediated activities. The compounds are typically subject to a Tyrosine Aminotransferase Assay (TAT assay), which assesses the ability of a test compound to inhibit the induction of tyrosine aminotransferase activity by dexamethasone. GR modulators that are suitable for the method disclosed herein have an $IC_{50}$ (half maximal inhibition concentration) of less than 10 micromolar. Other assays, including but not limited to those described below, can also be deployed to confirm the GR modulation activity of the compounds.

Cell-based assays which involve whole cells or cell fractions containing glucocorticoid receptors can also be used to assay for a test compound's binding or modulation of activity of the glucocorticoid receptor. Exemplary cell types that can be used according to the methods of the invention include, e.g., any mammalian cells including leukocytes such as neutrophils, monocytes, macrophages, eosinophils, basophils, mast cells, and lymphocytes, such as T cells and B cells, leukemia cells, Burkitt's lymphoma cells, tumor cells (including mouse mammary tumor virus cells), endothelial cells, fibroblasts, cardiac cells, muscle cells, breast tumor cells, ovarian cancer carcinomas, cervical carcinomas, glioblastomas, liver cells, kidney cells, and neuronal cells, as well as fungal cells, including yeast. Cells can be primary cells or tumor cells or other types of immortal cell lines. Of course, the glucocorticoid receptor can be expressed in cells that do not express an endogenous version of the glucocorticoid receptor.

In some embodiments, a reduction in signaling triggered by glucocorticoid receptor activation is used to identify glucocorticoid receptor modulators. Signaling activity of the glucocorticoid receptor can be determined in many ways. For example, downstream molecular events can be monitored to determine signaling activity. Downstream events include those activities or manifestations that occur as a result of stimulation of a glucocorticoid receptor. Exemplary downstream events useful in the functional evaluation of transcriptional activation and antagonism in unaltered cells include upregulation of a number of glucocorticoid response element (GRE)-dependent genes (PEPCK, tyrosine amino transferase, aromatase). In addition, specific cell types susceptible to GR activation may be used, such as osteocalcin expression in osteoblasts which is downregulated by glucocorticoids; primary hepatocytes which exhibit glucocorticoid mediated upregulation of PEPCK and glucose-6-phosphate (G-6-Pase)). GRE-mediated gene expression has also been demonstrated in transfected cell lines using well-known GRE-regulated sequences (e.g., the mouse mammary tumor virus promoter (MMTV) transfected upstream of a reporter gene construct). Examples of useful reporter gene constructs include luciferase (luc), alkaline phosphatase (ALP) and chloramphenicol acetyl transferase (CAT). The functional evaluation of transcriptional repression can be carried out in cell lines such as monocytes or human skin fibroblasts. Useful functional assays include those that measure IL-1beta stimulated IL-6 expression; the downregulation of collagenase, cyclooxygenase-2 and various chemokines (MCP-1, RANTES); LPS stimulated cytokine release, e.g., TNFα; or expression of genes regulated by NFkB or AP-1 transcription factors in transfected cell-lines.

Compounds that are tested in whole-cell assays can also be tested in a cytotoxicity assay. Cytotoxicity assays are used to determine the extent to which a perceived effect is due to non-glucocorticoid receptor binding cellular effects. In an exemplary embodiment, the cytotoxicity assay includes contacting a constitutively active cell with the test compound. Any decrease in cellular activity indicates a cytotoxic effect.

Further illustrative of the many assays which can be used to identify compositions utilized in the methods of the invention, are assays based on glucocorticoid activities in vivo. For example, assays that assess the ability of a putative GR modulator to inhibit uptake of 3H-thymidine into DNA in cells which are stimulated by glucocorticoids can be used. Alternatively, the putative GR modulator can complete with 3H-dexamethasone for binding to a hepatoma tissue culture GR (see, e.g., Choi, et al., *Steroids* 57:313-318, 1992). As another example, the ability of a putative GR modulator to block nuclear binding of 3H-dexamethasone-GR complex can be used (Alexandrova et al., *J. Steroid Biochem. Mol. Biol.* 41:723-725, 1992). To further identify putative GR modulators, kinetic assays able to discriminate between glucocorticoid agonists and modulators by means of receptor-binding kinetics can also be used (as described in Jones, *Biochem J.* 204:721-729, 1982).

In another illustrative example, the assay described by Daune, Molec. Pharm. 13:948-955, 1977; and in U.S. Pat. No. 4,386,085, can be used to identify anti-glucocorticoid activity. Briefly, the thymocytes of adrenalectomized rats are incubated in nutritive medium containing dexamethasone with the test compound (the putative GR modulator) at varying concentrations. $^3$H-uridine is added to the cell culture, which is further incubated, and the extent of incorporation of radiolabel into polynucleotide is measured. Glucocorticoid agonists decrease the amount of $^3$H-uridine incorporated. Thus, a GR antagonist will oppose this effect.

Pharmaceutical Compositions and Administration

In embodiments, the present invention provides methods for treating cancer comprising intermittent administration of a pharmaceutical composition including a pharmaceutically acceptable excipient and a heteroaryl-ketone fused azadecalin GRM, such as relacorilant, along with a cancer chemotherapy regimen. In embodiments, pharmaceutical compositions comprising relacorilant include those disclosed in U.S. Patent Publication 2020/0197372, the entire contents of which is hereby incorporated by reference in its entirety.

Any suitable GRM dose may be used in the methods and uses disclosed herein. The dose of GRM that is administered can be at least about 10 milligrams (mg) per day, about 25 mg/day, about 40 mg/day, about 50 mg/day, about 60 mg/day, about 70 mg/day, about 80 mg/day, about 100 mg/day, about 110 mg/day, about 120 mg/day, about 130 mg/day, about 140 mg/day, about 150 mg/day, about 160 mg/day, about 170 mg/day, about 180 mg/day, about 190 mg/day, about 200 mg/day, about 225 mg/day, about 250 mg/day, or more. In some embodiments, the GRM is administered in at least one dose on days in which it is administered to the cancer patient. In embodiments, the GRM can be administered in 1, 2, 3, 4, 5, 6, 7, 8, 9, 10 or more doses on days in which it is administered to the cancer patient. In embodiments, the GRM is administered orally in 1, 2, 3, 4, 5, 6, 7, 8, 9, 10 or more doses on days in which it is administered to the cancer patient.

After a pharmaceutical composition including a heteroaryl-ketone fused azadecalin GR modulator has been formulated in an acceptable carrier, it can be placed in an appropriate container and labeled for treatment of cancer, e.g., when administered along with a regimen including a cancer chemotherapeutic. For administration of a heteroaryl-ketone fused azadecalin GRM, such labeling would include, e.g., instructions concerning the amount, frequency and method of administration.

The duration of treatment with a heteroaryl-ketone fused azadecalin GRM and a cancer chemotherapeutic to treat cancer can vary according to the severity of the condition in a patient and the patient's response. In some embodiments, GRMs can be administered with a cancer chemotherapeutic regimen for a period of about 1 week to about 104 weeks (2 years), or about 4 weeks to about 80 weeks, or about 3 weeks to about 60 weeks. For example, these periods may include at least several days or one week in which the patient does not receive the GRM, at least one week in which the patient does not receive the cancer therapeutic, or at least one week in which the patient does not receive either the GRM or the cancer therapeutic.

For example, a cancer chemotherapeutic regimen may be a regimen in which a patient receives 1, 2, 3, or more cycles of chemotherapy, where the cycle of chemotherapy may include administration of a chemotherapy agent on one day a week for three consecutive weeks, followed by one (or more) weeks without administration of the chemotherapy agent. Administration of a GRM with such a cancer chemotherapeutic regimen may include administration of the GRM to the patient on the days that the patient receives the chemotherapy agent. Administration of a GRM with such a cancer chemotherapeutic regimen may include administration of the GRM to the patient on the days that the patient receives the chemotherapy agent, and on the day before, or the day after, or both the day before and the day after, the days that the patient received the chemotherapy agent.

Administration of the therapeutic compounds or agents to a patient will follow general protocols for the administration of such compounds, taking into account the toxicity, if any, of the therapy. Surgical intervention may also be applied in combination with the described therapy.

The present methods can be combined with other means of treatment such as surgery, radiation, targeted therapy, immunotherapy, use of growth factor inhibitors, or anti-angiogenic agents.

EXAMPLES

The following examples are provided by way of illustration only and not by way of limitation. Those of skill will readily recognize a variety of noncritical parameters which could be changed or modified to yield essentially similar results.

Example 1. Intermittent Administration of Relacorilant with Nab-Paclitaxel Improves Progression-Free Survival and Overall Survival in Platinum-Resistant Ovarian Cancer Patients Unless noted otherwise, the data and analyses presented herein are from the primary analysis based on 154 progression free survival (PFS) events and 76 overall survival (OS) events) recorded by Mar. 22, 2021 (interim, or initial, analysis). A further OS analysis was performed (as predetermined) after achieving at least 120 OS events (by Mar. 7, 2022). A subgroup analysis which excluded the 7 primary platinum-refractory patients from the intermittent relacorilant with nab-paclitaxel group and which excluded the 1 primary platinum-refractory patient from the comparator (nab-paclitaxel only) group was also performed.

The effect of addition of GRM administration to cancer chemotherapy treatments was investigated in a clinical trial. While daily GRM dosing could provide continuous antagonism of GR-mediated chemo-resistance pathways, higher doses of GRM administered intermittently might yield higher GR antagonism around times of greatest chemotherapy exposure. In order to determine if different GRM dosing administration schemes might have different effects on treatment outcomes, and if so, in order to determine which scheme might provide superior benefits, some patients were treated with continuous relacorilant administration, and other patients were treated with intermittent relacorilant administration.

A 3-arm, randomized, open-label, controlled Phase 2 study was undertaken in which clinical findings from patients receiving nab-paclitaxel were compared to such clinical findings from patients receiving relacorilant as well as nab-paclitaxel. This example presents results from this study, which showed that intermittent administration of relacorilant in combination with nab-paclitaxel administration improves progression-free survival (PFS) in cancer patients. Such patients included patients with recurrent platinum-resistant ovarian cancer and other cancers (including, patients with fallopian tube cancer, high grade serous or endometrioid epithelial ovarian cancer, or ovarian carcinosarcoma, and patients with primary peritoneal cancer). Patients were classified as platinum-refractory (those patients who did not response to platinum-based therapy or who relapse within one month of treatment by platinum-based therapy) or as platinum-resistant (those patients who relapsed within 6 months of platinum-based therapy). Patients enrolled in the study had received at least one line of therapy with evidence of cancer progression [recurrent] within 6 months after the last dose of platinum-based therapy (i.e., having a platinum-free interval of ≤6 months [platinum-resistant]), or progressive disease during or immediately after platinum-based therapy (i.e., platinum-refractory). Patients with primary platinum resistance (progression within 6 months of the last dose of first-line platinum-containing chemotherapy) were eligible for this study.

This study enrolled cancer patients, including those suffering from ovarian, fallopian tube, peritoneal, and other cancers, for comparison of nab-paclitaxel monotherapy to two methods of administration of relacorilant along with the nab-paclitaxel treatment. A schematic illustration of the clinical trial protocol is presented in FIG. 1. 178 patients with platinum-resistant or platinum-refractory ovarian, primary peritoneal, or fallopian tube cancer were randomized 1:1:1 to receive either nab-paclitaxel alone (nab-paclitaxel monotherapy; 60 patients, termed the "comparator" group), continuous relacorilant administration with nab-paclitaxel (58 patients, termed the "continuous" group), or intermittent relacorilant administration with nab-paclitaxel (60 patients, termed the "intermittent" group). All of the patients in these groups were treated with 28-day chemotherapy cycles where nab-paclitaxel was administered on days 1, 8, and 15.

Patients in the comparator group received 100 milligrams per meter squared (mg/m$^2$) nab-paclitaxel, and no relacorilant. The results from the comparator group were used as a basis of comparison with the other groups. Patients in the continuous group received once-daily doses of relacorilant (initially 100 mg per day (mg/day), with a discretionary dose increase to 150 mg/day allowed in cycle 2 or later for patients who appeared able to tolerate higher doses based on their response to initial 100 mg doses) while also receiving 80 mg/m$^2$ nab-paclitaxel on days 1, 8, and 15 of the 28-day cycle. (Dose escalation was governed as follows: If during the first cycle no intolerable Grade 2 nor any Grade 3 or 4 toxicities require dose reduction or omission of either relacorilant or nab-paclitaxel, then the relacorilant dose will be escalated to 125 mg once daily, beginning on Cycle 2 Day 1. For patients who escalate the relacorilant dose to 125 mg, if no intolerable Grade 2 nor any Grade 3 or 4 toxicities require dose reduction or omission of either relacorilant or nab-paclitaxel in Cycle 2, then the relacorilant dose will be escalated to 150 mg once daily, beginning on Cycle 3 Day 1. If the dose was not escalated at Cycle 1 or 2, then the dose should not be escalated in future cycles.

Patients in the intermittent group received 80 mg/m$^2$ nab-paclitaxel on days 1, 8, and 15 of the 28-day cycles, and received once-daily doses of 150 mg relacorilant on the day before, the day of, and the day after nab-paclitaxel administration (except that no relacorilant was administered to the patients on the day before the first nab-paclitaxel administration). That is, patients in the intermittent group received relacorilant at a dose of 150 mg once per day on days 1 and 2; once per day on days 7, 8, and 9; once per day on days 14, 15, and 16; and once again on day 28 during the monthly cycle in which nab-paclitaxel was administered on days 1, 8, and 15 of the monthly cycle.

Independent comparisons for the intermittent versus (vs.) comparator study arms and the continuous vs. comparator arms were performed. The primary endpoint of the study was progression-free survival as determined by the Response Evaluation Criteria in Solid Tumors ("RECIST") version 1.1 guidelines (available via the World Wide Web at the following URL: ctep.cancer.gov/protocolDevelopment/docs/recist_guideline.pdf). Secondary endpoints included objective response rate, duration of response, overall survival, and safety of the combined administration of nab-paclitaxel and relacorilant. All efficacy objectives and corresponding endpoints listed below, assessment for response and disease progression were assessed according to RECIST v1.1.

As noted above, patients enrolled in this study had received multiple lines of prior therapy (a median of 3 and up to 5 lines), including prior taxane, prior bevacizumab, and prior PARP inhibitor therapies. Many of the ovarian cancer patients in this study were platinum-resistant patients (and more than 35% were platinum-refractory). Primary platinum-refractory patients were over-represented in the intermittent arm. All but one patient had received prior taxane, more than half had previously received bevacizumab, and just over a third had previously received a PARP inhibitor. Further information about characteristics of the patients enrolled in the study, and patient responses to the treatments applied to them, is provided in FIG. 2 for the total number of patients (right-most column) and for each of the three groups intermittent dosing of relacorilant; continuous dosing of relacorilant; and dosing with nab-paclitaxel alone (comparator group) (data as of Mar. 22, 2021). Stratification factors were relapse within 6 months on the most recent taxane and the presence of ascites. Molecular profiling results were available for some patients. The fraction of patients in this subset having BRCA 1 or 2 mutations is presented at the bottom of the table in FIG. 2.

The exposures and peak concentrations of both nab-paclitaxel and of relacorilant were measured. Overall, there was large variability in the relacorilant and nab-paclitaxel exposures, which is consistent with the pharmacokinetic profile of both compounds and the out-patient nature of the study design. The overall range of nab-paclitaxel exposures was largely overlapping across all three groups. Evaluation of relacorilant and nab-paclitaxel exposures (as measured by AUC and $C_{max}$) versus safety endpoints showed largely overlapping exposures in the presence or absence of the adverse events.

FIG. 3 presents information regarding the disposition of the patients enrolled in the study as of Mar. 22, 2021. For example, FIG. 3 shows the percentage of patients who discontinued study treatment at some point during the study, whether treated with nab-paclitaxel alone (comparator), or with relacorilant and nab-paclitaxel (whether intermittent or continuous relacorilant). As expected, the majority of discontinuations were due to progression of disease and only about 10% were due to adverse events. In addition to the numbers and percentages of patients in each group who discontinued the study treatment, FIG. 3 provides numbers and percentages for those patients who discontinued treatment due to disease progression, due to an adverse event, due to death, or due to other causes.

FIG. 4 presents progression-free survival (PFS) times for the three groups of patients as of Mar. 22, 2021. Significantly, the hazard ratio (HR) of PFS was improved for patients receiving nab-paclitaxel plus intermittent relacorilant treatment as compared to the PFS for patients receiving nab-paclitaxel alone: that HR was 0.66 (95% CI:0.44-0.98). Patients receiving nab-paclitaxel and intermittent relacorilant ("intermittent") had a median PFS of 5.6 months, which was 1.8 months longer than the median PFS for patients treated with nab-paclitaxel alone ("comparator"). While the number of platinum-refractory patients was well balanced across all study arms, there were more primary platinum-refractory patients in the intermittent arm. An analysis excluding primary platinum-refractory patients, who have especially poor prognosis, showed an improved hazard ratio for PFS (0.64 vs 0.66) and a stronger trend toward improved overall survival with the intermittent regimen, with a hazard ratio of 0.55 and a P-value of 0.056. The subgroup of patients without primary platinum-refractory disease and with 1-3 prior lines of therapy ("phase 3 population") comprised 137 patients, of whom 46 received nab-paclitaxel (80 mg/m$^2$)+intermittent relacorilant (150 mg QD the day before, of, and after nab-paclitaxel) and 50 received nab-paclitaxel only (100 mg/m$^2$). Nab-paclitaxel was administered on days 1, 8, and 15 of each 28-day cycle. For the subgroup excluding patients with primary refractory disease and excluding patients who had received more than 3 prior lines of treatment, PFS for intermittent relacorilant+nab-paclitaxel versus nab-paclitaxel alone was improved with a HR 0.58, 95% CI 0.37-0.91, log-rank test P=0.0162; and a median PFS 5.6 vs 3.8 months.

The median PFS for the women in the continuous group was 1.5 months longer than for the comparator group; this PFS also shows numerical improvement as compared to nab-paclitaxel alone, with a hazard ratio of 0.83, but was not statistically significant at the P<0.05 level. Thus, these PFS results show that intermittent administration of relacorilant with nab-paclitaxel administration provided superior therapeutic benefit as compared to nab-paclitaxel administration alone.

In addition, as shown in FIG. 5, patient duration of response (DoR) was also significantly improved in patients receiving intermittent relacorilant with nab-paclitaxel as compared to nab-paclitaxel alone (data as of Mar. 22, 2021). "PR" indicates partial response, and "CR" indicates complete response for the patient represented by the individual horizontal bar in the figure. The median DoR was 5.55 months in the intermittent arm of the study, which was a significant improvement as compared to 3.65 months in the comparator arm (hazard ratio HR of 0.36; P-value=0.006). The arrows in FIG. 5 indicate those patients for whom the duration of response continues (the patient was still showing response at the end of the study period). For the subgroup excluding patients without primary refractory disease and excluding patients who had received more than 3 prior lines of treatment, DoR for intermittent relacorilant+nab-paclitaxel versus nab-paclitxael alone was improved with a HR 0.26, 95% CI 0.11-0.62, log-rank test P=0.0009; median DoR 5.6 vs 3.6 mo. Thus, these DoR results show that intermittent administration of relacorilant with nab-paclitaxel administration provided superior therapeutic benefit as compared to nab-paclitaxel administration alone.

As illustrated in FIG. 6, presenting data for the final OS analysis (128 OS events) up to the further, pre-defined cut-off date of Mar. 7, 2022, the group of patients receiving intermittent relacorilant along with nab-paclitaxel showed improved overall survival as compared to the group of patients receiving nab-paclitaxel alone. 59% of the group of patients receiving intermittent relacorilant along with nab-paclitaxel were still alive at 12 months, and 27% of these patients were still alive at 24 months, as compared to 51% and 14% (respectively) of the patients receiving only nab-paclitaxel. The Hazard Ratio (HR) calculated from the Kaplan-Meier curves shown in FIG. 6 is 0.67 (95% CI [0.43, 1.03], P=0.066) for the patients receiving intermittent relacorilant with nab-paclitaxel, as compared to the patients receiving nab-paclitaxel alone. Thus, patients receiving intermittent relacorilant and nab-paclitaxel had a 33% reduction in the risk of death as compared to patients receiving nab-paclitaxel alone. Patients receiving intermittent relacorilant had a median OS of 13.9 months (95% CI [11.1, 18.4]) as compared to a median OS of 12.2 months (95% CI [7.7, 15.3]) for those patients who received nab-paclitaxel only. The HR was 0.85 (95% CI [0.56, 1.29], P=0.447) for continuous relacorilant+nab-paclitaxel vs. nab-paclitaxel only (median OS of 11.3 (95% CI [7.5, 16.4]) months in the continuous relacorilant+nab-paclitaxel arm).

A subgroup analysis excluding primary platinum-refractory patients (7 from the intermittent relacorilant plus nab-paclitaxel group, and 1 from the comparator group) and patients who had received four or more prior lines of therapy showed a statistically significant improvement in OS for intermittent relacorilant+nab-paclitaxel vs nab-paclitaxel only with a HR of 0.52 (95% CI [0.37, 0.91], P=0.010), indicating a 48% reduction in the risk of death as compared to patients receiving nab-paclitaxel alone. These overall survival results demonstrate that intermittent administration of relacorilant with nab-paclitaxel administration provided superior therapeutic benefit as compared to nab-paclitaxel administration alone. In addition to the improvements in PFS and DoR observed at the primary analysis, the OS analysis confirmed the survival benefit of intermittent relacorilant+nab-paclitaxel compared to nab-paclitaxel only, particularly in patients who were not primary platinum refractory.

FIG. 7A tabulates for comparison the progression-free survival (PFS), objective response rate (ORR), duration of response (DoR), and overall survival (OS) observed in the three groups of patients during the study as of the initial cut-off date of Mar. 22, 2021. Patients who prior to the study had not responded to first-line platinum-based therapy were considered "primary platinum-refractory" patients; these patients have an especially poor prognosis. The PFS, ORR, DoR, and OS were calculated for all 178 patients in the study ("overall" columns), and also for the 167 patients who were not "primary platinum-refractory" patients ("Primary Platinum-Refractory Removed" columns). Both analyses showed that intermittent dosing of relacorilant during cycles of taxane chemotherapy administration significantly improved PFS and DoR as compared to taxane chemotherapy alone. OS was clearly improved for patients receiving intermittent relacorilant as compared to those receiving nab-paclitaxel alone; as shown in FIGS. 6 and 7B, the OS improvement was statistically significant for the group of patients that excluded primary platinum-refractory patients (see, e.g., HR for patients receiving intermittent relacorilant dosing as compared to nab-paclitaxel alone).

Thus, as discussed above, and as shown in FIG. 7A (presenting an initial analysis of the data that had been collected as of the initial cut-off date of Mar. 22, 2021), the women in the higher dose Intermittent arm experienced a significant improvement in progression free survival (median PFS: 5.6 months versus 3.8 months, hazard ratio: 0.66; p-value: <0.05) and a statistically significant improvement in the duration of response (DoR) relative to those in the Comparator arm (median DoR: 5.6 months versus 3.7 months, hazard ratio: 0.36; p-value: 0.006).

FIG. 7B tabulates the progression-free survival (PFS), duration of response (DoR), and overall survival (OS) data for the subgroup of patients without primary platinum-refractory disease who had received 1-3 prior lines of therapy. In this subgroup, greater improvement in PFS, DoR, and OS vs. nab-paclitaxel monotherapy was observed. Patients with primary platinum-refractory disease and those with greater than 3 prior lines of therapy have particularly poor prognosis and are commonly excluded from clinical trials. Patients with primary platinum-refractory disease were randomly overrepresented in the intermittent relacorilant dosing arm vs. nab-paclitaxel monotherapy (n=11 vs. n=1). The data cutoff date for the final OS analysis was Mar. 7, 2022. This later cut-off date was decided upon by the pre-determined criterion of reaching 120 OS "events" in the study. The updated OS results (updated as compared to the data presented in FIG. 7A), which data are also shown in FIG. 6A, were a median OS of 13.9 months for the patients treated with nab-paclitaxel and intermittent relacorilant, as compared to a median OS of 12.2 months for patients treated with nab-paclitaxel alone. This was an improvement in OS (HR 0.67; P=0.066), with a 33% reduction in the risk of death for patients treated with intermittent dosing of relacorilant plus nab-paclitaxel, as compared to those treated with nab-paclitaxel alone. As shown in FIG. 7C, showing the results for the subgroup obtained by excluding primary platinum-refractory patients and patients who had received four or more prior lines of therapy, there was a significant improvement in OS— a 48% reduction in the risk of death for (non-primary platinum-refractory) patients treated with intermittent dosing of relacorilant plus nab-paclitaxel, as compared to those treated with nab-paclitaxel alone (HR 0.52; P=0.010).

Analysis of a further subgroup, patients with/without prior bevacizumab, found improved PFS, OS, and DoR with intermittent relacorilant+nab-paclitaxel compared to nab-paclitaxel treatment alone in patients who had received prior bevacizumab, while objective response rates (ORR) were similar across all groups. Of the 178 women with recurrent, platinum-resistant/refractory ovarian, primary peritoneal, or fallopian tube cancer or ovarian carcinosarcoma with ≤4 prior lines of chemotherapy enrolled in this phase 2, open-label, randomized study of relacorilant+nab-paclitaxel versus nab-paclitaxel alone (NCT03776812), 105 had received prior bevacizumab and 73 had not received prior bevacizumab). Data for patients in this subgroup who received either nab-paclitaxel (80 mg/m$^2$)+intermittent relacorilant (150 mg QD (once daily) the day before, of, and after nab-paclitaxel) or nab-paclitaxel alone (100 mg/m$^2$) are presented in the following TABLE. Baseline characteristics in the 2 groups were generally balanced. While patients without prior bevacizumab were balanced between North America and Europe, 70% of patients who received prior bevacizumab were in Europe.

Intermittent relacorilant+nab-paclitaxel treatment also led to numerical improvement in PFS as compared to nab-paclitaxel treatment alone, for patients without prior bevacizumab.

FIG. 7D tabulates the progression-free survival (PFS), duration of response (DoR), and overall survival (OS) data for the further specified subgroup of patients a) without primary platinum-refractory disease, b) who had received 1-3 prior lines of therapy, and c) which prior lines of therapy included prior bevacizumab treatment. In this subgroup, even greater improvement in PFS, DoR, and OS was observed than that observed in the other subgroup analyses ((compare, e.g., FIG. 7B, for a group in which prior bevacizumab was not required). These results are also illustrated, for example, in the charts shown in FIGS. 4B and 6B.

Such improvements in OS, PFS, and DoR are remarkable, and this relacorilant treatment regimen is believed to be the first to show significant improvement in overall survival for a group of patients with recurrent platinum resistant ovarian cancer. Safety and tolerability of relacorilant plus nab-paclitaxel was comparable to nab-paclitaxel monotherapy.

Relacorilant treatment was safe, for both the intermittent and continuous groups, and was well tolerated by the patients. Safety and tolerability were comparable between

TABLE

|  | Prior bevacizumab | | No prior bevacizumab | |
|---|---|---|---|---|
|  | Intermittent RELA + NP (n = 31) | NP alone (n = 37) | Intermittent RELA + NP (n = 29) | NP alone (n = 23) |
| PFS | | | | |
| Number of Events, (%) | (24 (77.4%) | 36 (97.3%) | | |
| Median PFS (95% CI), mo | 7.2 (2.96, 7.39) | 3.71 (3.48, 5.49) | 5.4 (2.83, 5.68) | 3.8 (3.42, 5.52) |
| HR* (95% CI) | 0.44 (0.24, 0.78) | N/A | 0.91 (0.48, 1.72) | N/A |
| 2-sided P-value | 0.0046 | N/A | 0.7669 | N/A |
| OS | | | | |
| Number of events (%) | 18 (58.1%) | 28 (75/7%) | | |
| Median (95% CI), mo | 17.9 (11.89, NR) | 12.6 (6.93, 15.87) | 11.3 (8.71, 17.22) | 12.2 (8.41, 15.51) |
| HR* (95% CI) | 0.47 (0.24, 0.94) | N/A | 0.80 (0.42, 1.52) | N/A |
| 2-sided P-value | 0.0307 | N/A | 0.5014 | N/A |
| ORR | | | | |
| Patients with measurable disease at baseline, n | n = 27 | n = 30 | n = 29 | n = 23 |
| ORR in patients with measurable disease at baseline, n (%) | 11 (40.7%) | 10 (33.3%) | 9 (31.0%) | 9 (39.1%) |
| DoR | | | | |
| Number of events (%) | 7 (63.6%) | 10 (100%) | | |
| Patients with response, n | n = 11 | n = 10 | n = 9 | n = 9 |
| Median DoR (95% CI), mo | 5.6 (4.1, NR) | 3.4 (1.28, 3.71) | 3.8 (3.6, NR) | 3.8 (2.89, 5.13) |
| HR* (95% CI) | 0.25 (0.08, 0.83) | N/A | 0.47 (0.13, 1.68) | N/A |
| 2-sided P-value | 0.006 | N/A | 0.2342 | N/A |

$^1$Data cutoff date for the primary analysis: Mar. 22, 2021; applies to PFS and DoR.
$^2$P-values are nominal, no multiplicity adjustment applied.
$^3$Data cutoff date for the final (OS) analysis: Mar. 7, 2022.
*Comparing intermittent relacorilant + nab-paclitaxel versus nab-paclitaxel alone
"RELA" is relacorilant; "NP" is nab-paclitaxel, "mo" is months, "NR" not reached.

In this subgroup analysis, patients who had received prior bevacizumab had better OS (hazard ratio 0.47; p-value 0.03; median 17.9 months v. 12.6 in control arm), PFS (hazard ratio 0.44; p-value 0.005; median 7.2 months v. 3.7 in control arm), and DoR (hazard ratio 0.25; p-value 0.006; median 5.6 months v 3.4 in control arm) with intermittent relacorilant+nab-paclitaxel versus nab-paclitaxel alone. ORR, while numerically highest in the intermittent relacorilant+nab-paclitaxel group, was similar across all groups.

groups, with neutropenia being the most common adverse event of grade ≥3. Safety and tolerability of the three treatment regimens is illustrated in FIG. 8 (data as of Mar. 22, 2021). There were fewer serious (grade ≥3) peripheral neuropathies in the intermittent group than the comparator group. Per the study protocol, all patients receiving relacorilant with nab-paclitaxel received prophylactic granulocyte colony stimulating factor (GCSF), a treatment for reducing the risk of neutropenia, while patients receiving nab-paclitaxel monotherapy were given G-CSF per the clinical investigator's (treating physician's) standard practice.

Levels of mRNA expression for selected targets were also measured in some patients. Such analyses also confirmed that some glucocorticoid receptor target genes were suppressed by relacorilant and nab-paclitaxel treatments. A panel of 239 genes that are induced by the glucocorticoid prednisone was analyzed in whole blood samples obtained from some of the patients. 221 of these genes were suppressed in patients who received relacorilant+nab-paclitaxel (change from baseline to cycle 1 day 15), while these genes were relatively unchanged with nab-paclitaxel alone (FIG. 9B). For example, mRNA expression of one of the classic glucocorticoid-responsive genes, the serum and glucocorticoid-regulated kinase (SGK1), which is involved in cell survival, was measured. The left-side of FIG. 9C shows the change in expression in whole blood samples from baseline to cycle 1 day 15 for SGK1 (error bars are median and interquartile ranges). As shown in FIG. 9C, levels of mRNA encoding SGK1 in whole blood were reduced in patients receiving both relacorilant and nab-paclitaxel as compared to SGK1 mRNA levels in whole blood samples from patients receiving nab-paclitaxel alone ($P<0.0089$). SGK1 expression was suppressed by relacorilant+nab-paclitaxel, while there was no suppression of SGK1 gene expression in patients treated with nab-paclitaxel only. Of 239 genes previously shown to be GR target genes, 221 were suppressed after RELA+NP treatment. Significantly fewer GR target genes were suppressed by NP ($P<0.00001$). GR target genes that were suppressed by relacorilant+nab-paclitaxel but not by nab-paclitaxel alone included SGK1 ($P=0.0089$), GSK3B ($P=0.0045$), and PIK3CG ($P=0.0175$).

137 pre-treatment samples obtained from tumors from patients in this study were profiled for expression of 444 genes. Expression (mRNA) levels of all genes in the samples is shown with circles on the left-side portion of FIG. 9D. The expression of NR3C1 (the gene that encodes for the glucocorticoid receptor) in each tumor is shown on the right-side portion of FIG. 9D. The median expression levels for each of the 444 genes were first determined. The median for NR3C1 fell in the $83^{rd}$ percentile of the distribution of 444 median values. Thus, the expression of glucocorticoid receptor-encoding mRNA (NR3C1) was found to be high in ovarian cancer tumors as compared to the mRNA expression of all genes in the patients (FIG. 9D).

FIG. 9B presents comparisons of the levels of mRNA encoding the glucocorticoid receptor in ovarian cancer patients who received nab-paclitaxel alone as compared to those receiving relacorilant along with nab-paclitaxel. GR expression was observed in 96% of evaluable ovarian tumors in our phase 2 study. High GR expression was associated with poor response in the nab-paclitaxel-only arm. In contrast, high GR expression was associated with partial or complete response in both relacorilant+nab-paclitaxel arms. For patients with high GR, the rate of a partial or complete response was doubled in the relacorilant+nab-paclitaxel as compared to the nab-paclitaxel alone arm.

To summarize, this Example presents the first randomized, controlled, phase 2 trial of relacorilant+nab-paclitaxel in patients with ovarian and other cancers. The study included platinum-resistant and refractory patients with up to 5 prior lines of therapy. In this heavily pretreated population, substantial benefit was observed. Benefit was observed with intermittent relacorilant+nab-paclitaxel treatment vs. nab-paclitaxel monotherapy in the entire study population, including improved PFS, DoR, and a trend toward improved OS. Greater improvements in PFS, OS, and DoR with intermittent relacorilant+nab-paclitaxel were observed in subgroup analyses, particularly in women without primary platinum-refractory disease who had received ≤3 prior lines of therapy, including prior bevacizumab. Patients treated with intermittent relacorilant+nab-paclitaxel had significantly improved PFS and significantly improved DoR compared to patients receiving nab-paclitaxel alone. Remarkably, the patients receiving intermittent relacorilant experienced improved median overall survival as compared to patients receiving nab-paclitaxel alone; this OS improvement was significant for the group of patients who were not primary platinum-refractory patients. The safety profile of intermittent relacorilant+nab-paclitaxel was comparable to that of nab-paclitaxel alone. Thus, these results show that intermittent administration of relacorilant with nab-paclitaxel administration surprisingly provided superior therapeutic benefit as compared to nab-paclitaxel administration alone.

Example 2 Planned Phase III Clinical Trial Comparing Intermittent Relacorilant with Nab-Paclitaxel to Prior Treatments In view of the promising results showing increased overall survival (OS), increased progression-free survival (PFS), increased duration of response (DoR), without significant changes in safety and patient toleration of the treatments, Applicant presents a planned Phase III clinical study to confirm and extend these positive clinical results in this prophetic Example.

As illustrated in FIG. 10A, a clinical trial enrolls 360 patients suffering from high grade serous epithelial (Grade 3), High-grade (Grade 3) Endometrioid, and Carcinosarcoma with ≥30% endometroid epithelial tumor component, ovarian, primary peritoneal, or fallopian tube cancer, and who had disease progression 6 months or less after their last dose of platinum-based therapy. Women with recurrent ovarian, primary peritoneal, or fallopian tube cancer following at least one treatment, and which is resistant to platinum-based chemotherapy, including the following histological subtypes: High-grade (Grade 3) serous epithelial ovarian, primary peritoneal, or fallopian-tube carcinoma; High-grade (Grade 3) endometrioid carcinoma; and Carcinosarcoma with a ≥30% endometroid epithelial tumor component. These criteria are expected to exclude primary-platinum refractory patients from the study. Patients are treated according to either the experimental intermittent relacorilant administration protocol, or according to one of four chemotherapy treatment regimens chosen by their physician. The primary endpoint measured is progression free survival (PFS) by blinded independent central review (BICR) per RECIST v. 1.1. Secondary efficacy endpoints include overall survival (OS); PFS (by investigator) per RECIST v. 1.1, by best overall response (BOR); duration of response (DoR) per RECIST v. 1.1; objective response rate (ORR); clinical benefit rate per RECIST v. 1.1; and combined response according to RECIST v. 1.1. plus GCIG (Gynecological Cancer InterGroup) criteria. Safety endpoints include patient safety, patient quality of life (QOL), Ca-125 (a protein marker monitored in ovarian cancer patients), pharmacodynamics, and pharmacokinetics. Patients are randomized 1:1 to A) receive either intermittent relacorilant administration (150 mg orally) with nab-paclitaxel (80 mg/m$^2$; 180 patients), where nab-paclitaxel is administered on days 1, 8, and 15, and relacorilant is administered on days 1, 2, 7-9, 14-16, and 28 of a 28-day cycle, or B) "investigator's choice", in which the patients receive, per their treating physician, either liposomal doxorubicin (40 mg/m² intravenously (i.v.)) on day 1 of a 28-day cycle; paclitaxel (80 mg/m²; i.v.) on days 1, 8, 15, and 22 of a 28-day cycle; nab-paclitaxel (100 mg/m², i.v.) on days 1, 8, and 15 of a 28-day cycle; or topotecan, in which the treating physician may choose either administration of 4 mg/m², i.v. on days 1, 8, and 15 of a 28-day cycle or 1.25 mg/m² i.v. on Days 1-5 of each 21-day cycle. Arm B) of the study is the comparator arm of the study, in which patients do not receive relacorilant.

An example of such a clinical trial is illustrated in FIG. 10B. Informed by the subgroup analyses disclosed herein, a randomized, controlled, 2-arm, open-label, multicenter phase 3 study of intermittent relacorilant+nab-paclitaxel vs. nab-paclitaxel entitled ROSELLA has been initiated and is ongoing (NCT05257408). In particular, the ROSELLA trial will enroll patient who have previously received bevacizumab. This study is expected to enroll about 360 patients having high-grade, serous, epithelial, ovarian, primary peritoneal, or fallopian tube cancer, who have had from 1 to 3 prior lines of systemic anticancer therapy, of which one must have been bevacizumab treatment. The patients further will have exhibited disease progression less than or equal to 6 months after their last dose of platinum-based therapy; however, primary platinum-refractory patients will be excluded from the study.

Results of the Phase 3 clinical study are expected to include significant improvements in OS, PFS, DoR, and other measures of the treatments for patients in arm A), as compared to patients in arm B) not receiving intermittent relacorilant. No significant differences in safety and patient toleration of the treatments between arms A) (relacorilant+nab-paclitaxel) and B) (nab-paclitaxel alone) are expected.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

All patents, patent publications, patent applications, and publications cited in this specification are hereby incorporated by reference herein in their entireties as if each individual publication or patent application were specifically and individually indicated to be incorporated by reference. In addition, although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A method of treating cancer in a patient suffering from platinum-resistant ovarian, fallopian tube, uterine, cervical, vaginal, vulvar, or peritoneal cancer and having a cancerous tumor that expresses high levels of mRNA encoding the glucocorticoid receptor gene NR3C1, comprising:
   a) determining that the expression level of mRNA encoding the glucocorticoid receptor gene NR3C1 in a sample of said cancerous tumor is higher than the median level of mRNA expression in said sample of the cancerous tumor, wherein
      i) said cancerous tumor is selected form the group consisting of ovarian, fallopian tube, uterine, cervical, vaginal, vulvar, and peritoneal cancer;
      ii) said patient suffered from progression of said cancer within six months after receiving a platinum-based cancer chemotherapy treatment; and
      iii) the patient has received at least one prior systemic cancer treatment comprising administration of bevacizumab; and
   b) administering to the patient a cancer chemotherapy agent comprising a taxane,
   wherein said taxane cancer chemotherapy agent is selected from the group of taxane cancer chemotherapy agents consisting of paclitaxel, nab-paclitaxel, docetaxel, larotaxel, tesetaxel, cabazitaxel, and ortataxel,
   said taxane administration comprising administration according to a cancer chemotherapy dosing schedule,
   said cancer chemotherapy dosing schedule requiring that there be at least one day without administration of said taxane cancer chemotherapy agent between days on which the taxane cancer chemotherapy agent is administered to the patient;
   c) intermittently administering to the patient an effective amount of the heteroaryl ketone fused azadecalin glucocorticoid receptor modulator compound (R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone ("relacorilant"), which has the following structure:

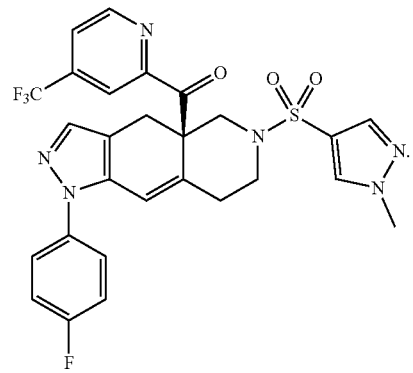 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

wherein said intermittent administration comprises administration of said relacorilant on the day before, the day of, and the day after said taxane cancer chemotherapy agent is administered to the patient, thereby treating said platinum-resistant center in the patient i) identified as hosting a cancerous tumor that expresses high levels of mRNA encoding the glucocorticoid receptor gene NR3C1 as compared to the median level of mRNA expression in the cancerous tumor, ii) who suffered from disease progression within six months after receiving a platinum-based cancer chemotherapy treatment, and iii) who has received at least one prior systemic cancer treatment comprising administration of bevacizumab.

2. The method of claim 1, wherein said patient has received no more than three prior systemic cancer treatments, at least one of which prior systemic cancer treatments comprised administration of bevacizumab.

3. The method of claim 1, wherein said cancer is ovarian cancer.

4. The method of claim 1, wherein the taxane cancer chemotherapy agent is a taxane containing paclitaxel.

5. The method of claim 1, wherein the taxane cancer chemotherapy agent is nab-paclitaxel.

6. The method of claim 1, wherein said cancer chemotherapy dosing schedule comprises administration of said cancer chemotherapy agent on a first day, and again on a day seven days after said first day, without administration of said cancer chemotherapy agent on days between the first and said day seven days after said first day.

7. The method of claim 1, wherein said cancer chemotherapy agent is administered to the patient according to the cancer chemotherapy dosing schedule for three consecutive weeks.

8. The method of claim 7, wherein said taxane cancer chemotherapy agent is administered to the patient according to the cancer chemotherapy dosing schedule for three consecutive weeks, and then not administered the week following the last of said three consecutive weeks.

9. The method of claim 7, wherein said taxane cancer chemotherapy agent is administered to the patient according to the cancer chemotherapy dosing schedule for three consecutive weeks, and then not administered the week following the last of said three consecutive weeks, and then said weekly dosing regimen is repeated for three further consecutive weeks.

10. The method of claim 1, wherein said patient does not suffer from platinum-refractory disease, wherein platinum-refractory disease is identified by the progression of the cancer within one month of the patient receiving a platinum-based cancer therapy.

11. The method of claim 1, wherein said patient does not suffer from primary platinum-refractory disease, wherein primary platinum-refractory disease is identified by the progression of the cancer within one month of the patient receiving their first treatment of a platinum-based cancer therapy.

12. The method of claim 1, wherein said level of mRNA encoding the glucocorticoid receptor gene NR3C1 comprises a level of at least about the $80^{th}$ percentile of mRNA expression levels of genes expressed in said cancerous tumor.

13. The method of claim 1, wherein said taxane is nab-paclitaxel and administered at a dose of about 80 milligrams per square meter ($mg/m^2$).

14. The method of claim 1, wherein said effective amount of relacorilant is a dose of about 150 milligrams (mg) of relacorilant.

* * * * *

UNITED STATES PATENT AND TRADEMARK OFFICE
CERTIFICATE OF CORRECTION

PATENT NO. : 12,109,272 B2
APPLICATION NO. : 17/902701
DATED : October 8, 2024
INVENTOR(S) : Stacie Shepherd and Joseph K. Belanoff It is certified that error appears in the above-identified patent and that said Letters Patent is hereby corrected as shown below:

In the Claims

Column 33, Line 65, Claim 1: please delete the word "form" and insert --from--.

Column 34, Line 50, Claim 1: please delete the word "center" and insert --cancer--.

Column 35, Line 5, Claim 6: insert the word --taxane-- at the beginning of the line.

Column 35, Line 7, Claim 6: insert the word --taxane-- at the beginning of the line.

Column 35, Line 7, Claim 6: insert the word --day-- after the word first.

Column 35, Line 9, Claim 7: insert the word --taxane-- after the word said.

Signed and Sealed this
Twenty-sixth Day of November, 2024

Katherine Kelly Vidal
*Director of the United States Patent and Trademark Office*